(12) United States Patent
Gang et al.

(10) Patent No.: US 10,968,468 B2
(45) Date of Patent: Apr. 6, 2021

(54) PRODUCTION OF HYDROXYLATED AND METHOXYLATED FLAVONOIDS IN YEAST BY EXPRESSION SPECIFIC ENZYMES

(71) Applicant: Washington State University, Pullman, WA (US)

(72) Inventors: David Gang, Moscow, ID (US); Anna Berim, Pullman, WA (US)

(73) Assignee: Washington State University, Pullman, WA (US)

( * ) Notice: Subject to any disclaimer, the term of this patent is extended or adjusted under 35 U.S.C. 154(b) by 56 days.

(21) Appl. No.: 16/397,371

(22) Filed: Apr. 29, 2019

(65) Prior Publication Data

US 2019/0330669 A1    Oct. 31, 2019

Related U.S. Application Data

(60) Provisional application No. 62/664,858, filed on Apr. 30, 2018.

(51) Int. Cl.
*C12P 17/06* (2006.01)
*C12N 9/10* (2006.01)
*C12N 15/81* (2006.01)
*C12N 1/16* (2006.01)

(52) U.S. Cl.
CPC ............... *C12P 17/06* (2013.01); *C12N 1/16* (2013.01); *C12N 9/1007* (2013.01); *C12N 15/81* (2013.01); *C12Y 201/01042* (2013.01); *C12Y 201/01231* (2013.01)

(58) Field of Classification Search
None
See application file for complete search history.

*Primary Examiner* — Suzanne M Noakes
*Assistant Examiner* — Jae W Lee
(74) *Attorney, Agent, or Firm* — W&C IP

(57) ABSTRACT

Recombinant yeast that are genetically modified to contain and express genes or gene pathways that produce hydroxylated and/or methoxylated flavonoids are provided. The genes or gene pathways are derived from plants, for example, from sweet basil (*Ocimum basilicum*) and the hydroxylated and/or methoxylated flavonoids include, for example, 6-methoxylated naringenin, 6-methoxylated luteolin and 6-methoxylated kaempferol.

16 Claims, 16 Drawing Sheets

Specification includes a Sequence Listing.

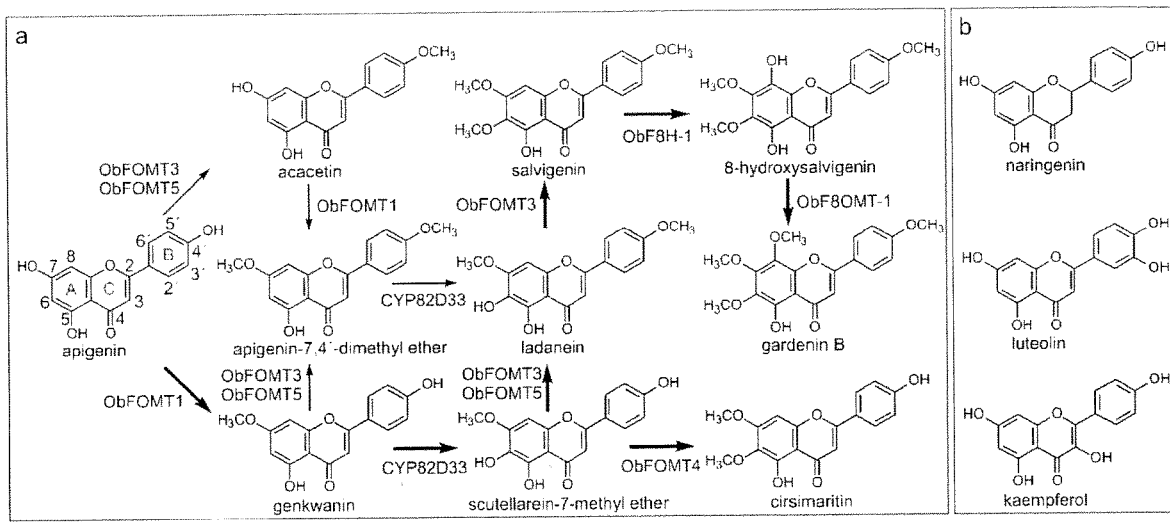
Figure 1A
Figure 1B
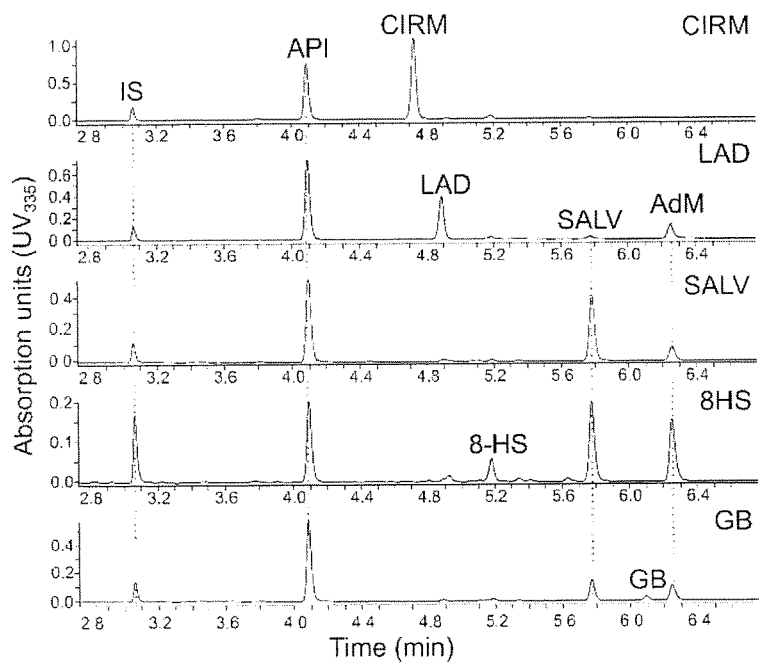
Figure 2

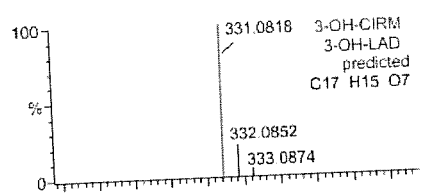
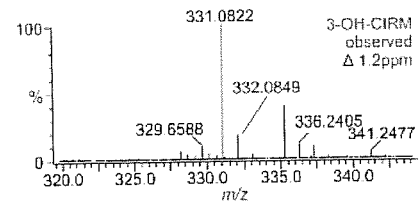
Figure 16D
Figure 16E
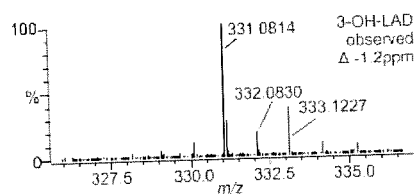
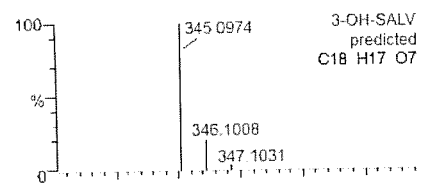
Figure 16F
Figure 16G
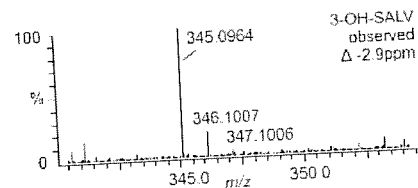
Figure 16H

SEQUENCE LISTING

```
<160> NUMBER OF SEQ ID NOS: 27

<210> SEQ ID NO 1
<211> LENGTH: 340
<212> TYPE: PRT
<213> ORGANISM: Ocimum basilicum

<400> SEQUENCE: 1

Met Gly Arg Asp Glu Glu Ala Ala Ala Gln Ala Glu Ala Trp Asn His
1               5                   10                  15

Gly Phe Gly Phe Ile Lys Thr Ser Val Ile Lys Thr Ala Ile Glu Leu
            20                  25                  30

Glu Ile Pro Asp Ile Leu His Asn Gln Gly Gly Pro Leu Ser Leu Ser
        35                  40                  45

Ala Leu Ser Ser Ala Val Gly Val Pro Pro Asp Arg Leu His Arg Ile
    50                  55                  60

Met Arg Phe Leu Ala His His Gly Val Ser Lys Lys Thr Ala Ser Pro
65                  70                  75                  80

Pro Gly Glu Ser Asp Tyr Tyr Tyr Ala Glu Thr Ala Val Ser Arg Ser
                85                  90                  95

Leu Thr Lys Asp Asn Leu Gly Pro Phe Val Leu Leu Gln Gly Ala Gln
            100                 105                 110

Arg Gly Pro Ser Ala Cys Ile Thr Ala Gln Gly Leu Lys Ser Arg Glu
        115                 120                 125

Arg Pro Gly Val Glu Glu Leu Gly Ser Asp Pro Leu Tyr Glu Asp Pro
    130                 135                 140

Ile Phe Thr Glu Lys Val Phe Arg Asp Ala Met Thr Cys His Ala Arg
145                 150                 155                 160

Val Thr Thr Ser Ala Val Ile Glu Asn Tyr Gly Glu Gly Phe Arg Gly
                165                 170                 175

Val Gly Ser Leu Val Asp Val Gly Gly Ser Tyr Gly Met Thr Leu Gly
            180                 185                 190

Met Leu Val Glu Ala Phe Pro Trp Ile Arg Gly Ile Cys Tyr Asp Leu
        195                 200                 205
```

```
Pro Pro Val Ala Lys Ala Lys Pro Leu His Gly Val Glu Phe Val
    210                 215                 220

Ala Gly Ser Met Phe Glu Ser Val Pro Lys Ala Asp Val Ile Met Leu
225                 230                 235                 240

Met Phe Val Leu His Asn Trp Ser Asp Asn Glu Cys Ile Asp Ile Leu
                245                 250                 255

Lys Arg Cys Lys Glu Ala Ile Pro Ala Glu Thr Gly Arg Leu Met Ile
            260                 265                 270

Ile Asp Ala Ile Ile Asp Glu Asp Gly Glu Gly Asp Glu Phe Ala Gly
        275                 280                 285

Ala Arg Leu Gly Leu Asp Val Thr Met Met Ala Val Thr Tyr Glu Gly
    290                 295                 300

Lys Glu Arg Thr His Arg Glu Trp Ala Tyr Ile Leu Thr Glu Ala Gly
305                 310                 315                 320

Phe Arg Lys Tyr Val Val Asn Asn Ile Lys Ala Leu Glu Ser Leu Ile
                325                 330                 335

Glu Ala Tyr Pro
            340

<210> SEQ ID NO 2
<211> LENGTH: 336
<212> TYPE: PRT
<213> ORGANISM: Ocimum basilicum

<400> SEQUENCE: 2

Met Ala Val Asp Lys Glu Val Gln Leu His Ala Gln Ala Trp Glu His
1               5                   10                  15

Ala Leu Ser Tyr Ile Asn Ser Thr Ala Leu Ser Ala Ala Val Glu Leu
            20                  25                  30

Glu Ile Pro Asp Ile Leu Glu Asp His Gly Gly Leu Met Ser Leu Ser
        35                  40                  45

Glu Leu Ser Ala Ala Ser Gly Cys Pro Arg Glu Pro Leu Tyr Arg Leu
    50                  55                  60

Met Arg Phe Leu Ile Phe His Gly Ile Phe Thr Lys Ser Asp Asp Cys
65                  70                  75                  80

Tyr Ala Gln Ser Pro Leu Ser Arg Leu Phe Thr Arg Glu Asn Leu Gly
                85                  90                  95

Pro Tyr Met Leu Met Gln Ala Thr Pro Val Thr Arg Ser Pro Ala Gly
            100                 105                 110

Leu Ser Gly Glu Ala Leu Lys Thr Gly Thr Ser Leu Tyr Leu Lys Ser
        115                 120                 125

Ile Arg Gly Glu Asp Ser Trp Ser Asp Pro Ala Tyr Gly Tyr His Met
    130                 135                 140

Lys Ala Phe Thr Asn Ala Met Ile Ala His Ala Arg Leu Thr Ala Ala
145                 150                 155                 160

Ala Ile Val Ser Asn Tyr Pro Ala Ala Phe Asp Gly Leu Arg Ser Val
                165                 170                 175

Val Asp Val Gly Gly Arg His Gly Thr Ala Ile Gly Arg Leu Val Glu
            180                 185                 190

Ala Phe Pro Trp Val Arg Gly Ile Ala Phe Asp Leu Pro Glu Ile Val
        195                 200                 205

Ala Asp Ala Pro Pro Arg Lys Gly Val Asp Phe Val Gly Gly Asp Met
    210                 215                 220

Phe Glu Ser Val Pro Lys Ala Asp Ala Val Met Leu Met Trp Ile Leu
```

```
            225                 230                 235                 240

His Asp Trp Ser Asp Asp Lys Cys Ile Glu Ile Leu Lys Lys Cys Lys
                245                 250                 255

Glu Ala Ile Pro Ala Ser Thr Gly Lys Val Met Ile Val Asp Ala Ile
                260                 265                 270

Ile Asn Glu Asp Gly Glu Gly Asp Glu Phe Ser Gly Ala Arg Leu Ser
                275                 280                 285

Leu Asp Met Ile Met Leu Ala Val Met Ala Gln Gly Lys Glu Arg Thr
            290                 295                 300

Tyr Lys Glu Trp Val His Leu Leu Asn Glu Ala Gly Phe Ser Lys His
305                 310                 315                 320

Thr Val Lys Asn Ile Lys Ser Ile Glu Ser Val Ile Glu Ala Tyr Pro
                325                 330                 335

<210> SEQ ID NO 3
<211> LENGTH: 336
<212> TYPE: PRT
<213> ORGANISM: Ocimum basilicum

<400> SEQUENCE: 3

Met Ala Val Asp Lys Glu Val Glu Leu His Ala Gln Ala Trp Asp His
1               5                   10                  15

Ala Leu Ser Tyr Ile Thr Pro Thr Ala Leu Ser Ala Ala Val Glu Leu
                20                  25                  30

Glu Ile Pro Asp Ile Leu Glu Asp His Gly Gly Leu Met Ser Leu Ser
            35                  40                  45

Glu Leu Ser Ala Ala Ser Gly Cys Pro Arg Glu Pro Leu Tyr Arg Leu
50                  55                  60

Met Arg Phe Leu Ile Phe His Gly Ile Phe Thr Lys Ser Asn Asp Cys
65                  70                  75                  80

Tyr Ala Gln Ser Pro Leu Ser Arg Val Phe Thr Arg Glu Asn Leu Gly
                85                  90                  95

Pro Tyr Met Leu Met Gln Ala Thr Pro Val Thr Arg Ser Pro Ala Gly
            100                 105                 110

Leu Ser Gly Glu Ala Leu Lys Thr Gly Thr Pro Leu Tyr Leu Lys Ser
            115                 120                 125

Ile Arg Gly Glu Asp Ser Trp Asn Asp Pro Ala Tyr Gly Phe His Met
130                 135                 140

Arg Ala Phe Thr Asn Gly Met Ala Ala His Ala Arg Leu Thr Ala Ala
145                 150                 155                 160

Ala Ile Val Thr Asn Tyr Pro Thr Ala Phe Asn Gly Val Arg Ser Val
                165                 170                 175

Val Asp Val Gly Gly Arg His Gly Met Ala Ile Gly Lys Leu Val Glu
            180                 185                 190

Ala Phe Pro Trp Val Arg Gly Ile Ala Phe Asp Leu Pro Glu Val Val
            195                 200                 205

Ala Asp Ala Pro Pro Arg Lys Gly Val Asp Phe Val Gly Gly Asp Met
210                 215                 220

Phe Glu Ser Leu Pro Lys Ala Asp Ala Val Met Leu Met Trp Val Leu
225                 230                 235                 240

His Asp Trp Ser Asp Asp Lys Cys Ile Glu Ile Leu Lys Lys Cys Lys
                245                 250                 255

Glu Ala Ile Pro Thr Ser Thr Gly Lys Val Met Ile Val Asp Ala Ile
            260                 265                 270
```

```
Ile Asn Glu Gly Glu Gly Asp Glu Phe Ser Gly Ala Arg Leu Ser
            275                 280                 285

Leu Asp Met Thr Met Met Ala Met Thr Thr Gln Gly Lys Glu Arg Ser
        290                 295                 300

Tyr Lys Glu Trp Val His Leu Leu Asn Glu Ala Gly Phe Ser Lys His
305                 310                 315                 320

Thr Val Lys Asn Ile Lys Thr Ile Glu Phe Val Ile Glu Ala Tyr Pro
                325                 330                 335

<210> SEQ ID NO 4
<211> LENGTH: 336
<212> TYPE: PRT
<213> ORGANISM: Ocimum basilicum

<400> SEQUENCE: 4

Met Val Ala Asp Glu Glu Ala Gln Leu His Ala Gln Ala Trp Asp His
1               5                   10                  15

Ala Leu Ser Tyr Ile Lys Pro Thr Ala Leu Ser Ala Ala Val Glu Leu
            20                  25                  30

Glu Ile Pro Asp Ile Leu Glu Asn His Gly Gly Pro Met Thr Leu Ser
        35                  40                  45

Glu Leu Ser Ala Ala Ser Gly Cys Pro Arg Glu Pro Leu Tyr Arg Leu
    50                  55                  60

Met Arg Phe Leu Ile Phe His Gly Ile Phe Thr Lys Ser Asp Asp Cys
65                  70                  75                  80

Tyr Ala Gln Ser Pro Leu Ser Arg Leu Phe Thr Thr Glu Asn Leu Gly
                85                  90                  95

Pro Tyr Met Leu Met Gln Ala Thr Pro Val Thr Arg Cys Pro Thr Gly
            100                 105                 110

Leu Ser Gly Glu Ala Leu Lys Thr Gly Thr Ser Leu Tyr Leu Lys Ser
        115                 120                 125

Ile Arg Gly Glu Asp Ser Trp Ser Asp Pro Ala Tyr Gly Tyr His Met
    130                 135                 140

Lys Ala Phe Thr Asn Ala Met Thr Ala His Ala Arg Leu Thr Ala Ala
145                 150                 155                 160

Ala Ile Val Arg Asn Tyr Pro Ala Ala Phe Asp Gly Val Gln Ser Val
                165                 170                 175

Val Asp Val Gly Ser Arg His Gly Thr Ala Ile Gly Lys Leu Val Glu
            180                 185                 190

Ala Phe Pro Trp Val Arg Gly Ile Ala Phe Asp Leu Pro Glu Ile Val
        195                 200                 205

Ala Asp Ala Pro Pro Arg Lys Gly Val Asp Phe Val Gly Gly Asp Met
    210                 215                 220

Phe Glu Ser Val Pro Lys Ala Asp Ala Val Met Leu Met Trp Ile Leu
225                 230                 235                 240

His Asp Trp Ser Asp Asp Lys Cys Ile Glu Ile Leu Lys Lys Cys Lys
                245                 250                 255

Glu Ala Ile Pro Ala Asn Ile Gly Lys Val Met Ile Val Asp Ala Ile
            260                 265                 270

Ile Asn Glu Asp Gly Glu Gly Asp Glu Phe Ser Gly Thr Arg Leu Ser
        275                 280                 285

Leu Asp Met Ile Met Leu Ala Val Met Ala Gln Gly Lys Glu Arg Thr
    290                 295                 300

Tyr Lys Glu Trp Val His Leu Leu Asn Glu Ala Gly Phe Ser Lys His
305                 310                 315                 320
```

Thr Ile Lys Asn Ile Lys Ala Met Glu Phe Val Ile Glu Ala Tyr Pro
                325                 330                 335

<210> SEQ ID NO 5
<211> LENGTH: 359
<212> TYPE: PRT
<213> ORGANISM: Ocimum basilicum

<400> SEQUENCE: 5

Met Pro Ser Ser Ser Gly Val Asp Ser Thr Gln Glu Leu Leu Asp Ala
1               5                   10                  15

Gln Ala His Ile Trp Asn His Ile Phe Asn His Ile Asn Ser Met Thr
                20                  25                  30

Leu Lys Trp Ala Val Gln Leu Gly Ile Pro Asp Ile Ile His Lys His
                35                  40                  45

Asp Lys Pro Met Thr Leu Ser Gln Leu Ala Asp Ala Ile Pro Ile Asn
            50                  55                  60

Arg Ala Lys Ser Asp Ala Leu His Arg Ile Met Arg Ile Leu Val His
65                  70                  75                  80

Ser Lys Phe Phe Asp Arg Val Arg Thr Leu Pro Asn Glu Gly Glu Ala
                85                  90                  95

Tyr Cys Leu Thr Arg Ala Ser Arg Leu Leu Leu Arg Asp Glu Pro Leu
                100                 105                 110

Ser Leu Thr Pro Phe Ala Leu Ala Val Leu Asp Glu Asp Leu Met Gly
            115                 120                 125

Thr Phe His Cys Val Pro Glu Trp Phe Gly Asn Glu Cys Pro Ser Pro
130                 135                 140

Leu Glu Phe Lys His Glu Lys Ser Ile Arg Glu Phe Ala Glu Asn Asn
145                 150                 155                 160

Gln Arg Trp Ser Leu Leu Phe Asn Glu Gly Met Ala Asn Asp Ala Arg
                165                 170                 175

Leu Val Gly Ser Ile Leu Ala Lys Glu Ser Arg Lys Val Phe Glu Gly
                180                 185                 190

Leu Glu Thr Met Val Asp Val Gly Gly Gly Thr Gly Met Val Ser Lys
            195                 200                 205

Ala Ile Val Asp Ala Phe Pro Gly Met Lys Gly Ile Val Leu Asp Leu
210                 215                 220

Pro Tyr Val Val Ser Gly Leu Lys Gly Ser Gly Asn Leu Arg Tyr Val
225                 230                 235                 240

Gly Gly Asp Met Phe His Ser Val Pro Pro Ala Asp Ala Val Phe Leu
                245                 250                 255

Lys Trp Ile Leu His Asn Trp Ser Asp Asp Glu Cys Ile Lys Ile Leu
                260                 265                 270

Glu Lys Cys Lys Glu Ala Ile Thr Thr Ser Lys Asn Met Lys Gly Gly
            275                 280                 285

Lys Val Ile Ile Val Asp Met Ile Leu Gly Tyr Glu Lys Gln Gln Asp
290                 295                 300

Glu Ala Val Glu Thr Gln Leu Phe Phe Asp Met Met Met Thr Thr
305                 310                 315                 320

Leu Thr Gly Lys Glu Arg Thr Glu Gln Glu Trp Ala Lys Ile Phe Phe
                325                 330                 335

Ala Ala Gly Phe Lys Thr Tyr Lys Ile Tyr Pro Leu Leu Gly Leu Arg
                340                 345                 350

Ser Leu Ile Glu Val Phe Pro

355

<210> SEQ ID NO 6
<211> LENGTH: 534
<212> TYPE: PRT
<213> ORGANISM: Ocimum basilicum

<400> SEQUENCE: 6

Met Glu Phe Ile Ser Phe Val Tyr Thr Leu Ile Ala Phe Ser Ser Leu
1               5                   10                  15

Leu Tyr Phe Tyr Leu Ile Trp Ser Glu Ser Ala Lys Pro Lys Thr Thr
                20                  25                  30

Thr His Lys Ala Pro Pro Glu Ala Ser Gly Ala Trp Pro Val Ile Gly
            35                  40                  45

His Leu Arg Ile Met Ser Gly His Pro Ser Ala Gly Ile Pro His Val
    50                  55                  60

Asn Leu Gly Met Leu Ala Asp Lys His Gly Pro Ile Phe Ser Ile Arg
65                  70                  75                  80

Leu Gly Val His Arg Val Val Val Ser Pro Glu Val Ile Lys
                85                  90                  95

Glu Leu Phe Thr Thr Asn Asp Val Ala Val Ser Ser Arg Pro Ser Val
            100                 105                 110

Lys Ala Gly Lys His Leu Ala Tyr Asp Asn Ala Met Leu Gly Phe Ala
        115                 120                 125

Ser Tyr Gly Ala Tyr Trp Arg Gln Leu Arg Lys Ile Val Ser Leu Glu
    130                 135                 140

Leu Leu Ser Asn Arg Arg Leu Glu Leu Gln Ser His Val Ser Met Ser
145                 150                 155                 160

Glu Thr Gly Gln Phe Val Lys Glu Leu Tyr Lys Leu Trp Glu Lys Lys
                165                 170                 175

Lys Ser Asp Gly Ser Gly Thr Glu Val Gly Glu Val Val Asp
            180                 185                 190

Met Lys Arg Trp Leu Gly Glu Leu Asn Met Asn Val Val Met Arg Met
    195                 200                 205

Val Ala Gly Lys Arg Phe Gly Ser Gly Asp Asn Ala Glu Glu Thr Lys
    210                 215                 220

Arg Cys Arg Arg Val Met Gly Asp Phe Phe Tyr Leu Ala Gly Phe Phe
225                 230                 235                 240

Val Pro Ala Asp Ala Leu Pro Tyr Leu Gly Trp Leu Asp Leu Gly Gly
                245                 250                 255

His Glu Lys Arg Met Lys Lys Ala Ala Lys Glu Leu Asp Glu Val Val
            260                 265                 270

Gly Glu Trp Leu Ala Glu His Arg Glu Arg Glu Phe Ser Gly Glu Gly
    275                 280                 285

Lys Ala Gln Asp Phe Met Asp Val Met Ile Ser Val Val Lys Gly Ala
    290                 295                 300

Asp Leu Gln Cys Glu Phe Asp Val Asp Thr Ile Ile Lys Ala Thr Cys
305                 310                 315                 320

Gly Thr Leu Ile Ala Gly Gly Thr Asp Thr Thr Ala Val Val Phe Val
                325                 330                 335

Trp Ala Leu Ser Leu Leu Leu Asn His Ser His Val Leu Lys Lys Ala
            340                 345                 350

Gln Gln Glu Leu Asp Lys His Val Gly Lys Asp Arg Arg Val Lys Glu
    355                 360                 365

```
Ser Asp Leu Asn Asn Leu Ile Tyr Leu Gln Ala Ile Val Lys Glu Thr
    370                 375                 380

Leu Arg Leu Tyr Pro Pro Gly Pro Leu Ala Gly Thr Arg Arg Phe Thr
385                 390                 395                 400

Glu Asp Cys Val Val Gly Gly Tyr Tyr Ile Pro Lys Asp Thr Trp Leu
                405                 410                 415

Ile Val Asn Leu Trp Lys Leu Gln Arg Asp Pro Arg Val Trp Ser Asp
            420                 425                 430

Pro Leu Glu Phe Arg Pro Glu Arg Phe Leu Ala Gly Asp Lys Thr Phe
                435                 440                 445

Asp Val Lys Gly Gln Asp Phe Glu Leu Ile Pro Phe Gly Ala Gly Arg
450                 455                 460

Arg Ile Cys Pro Gly Leu Ser Phe Gly Leu Gln Met Leu His Leu Val
465                 470                 475                 480

Leu Ala Ser Leu Leu Gln Ala Phe Asp Met Ser Thr Val Ser Asp Glu
                485                 490                 495

Ala Val Asp Met Ser Glu Ser Ala Gly Leu Thr Asn Met Lys Ala Thr
                500                 505                 510

Pro Leu Asp Val Val Thr Pro Arg Leu Pro Pro Arg Leu Tyr Asn
            515                 520                 525

Glu Ile Val Glu Ile Tyr
            530
```

<210> SEQ ID NO 7
<211> LENGTH: 523
<212> TYPE: PRT
<213> ORGANISM: Ocimum basilicum

<400> SEQUENCE: 7

```
Met Pro Phe Pro Met Glu Val Leu Gln Ala Ser Ser Leu Ser Phe Pro
1               5                   10                  15

Leu Leu Arg Arg His Ser Arg Asn Asn Leu Ile Asn Lys Phe Arg Asn
                20                  25                  30

Pro Thr Leu Pro Arg Ile Asp Ile Pro Arg Gln Asn Ile Asp Leu Lys
            35                  40                  45

Thr Phe Ala Ala Thr Thr Pro Thr Val Ala Cys Pro Pro Ser Asp Pro
        50                  55                  60

Glu Ile Ile Pro Glu Lys Lys Glu Asp Lys Phe Asp Trp Tyr Glu Asn
65                  70                  75                  80

Trp Tyr Pro Val Ala Thr Val Cys Asp Leu Asp Lys Arg Arg Pro His
                85                  90                  95

Gly Arg Lys Val Ile Gly Ile Asp Val Val Trp Trp Asp Arg Lys
                100                 105                 110

Glu Asn Ala Trp Lys Val Phe Asp Asp Thr Cys Pro His Arg Leu Ala
            115                 120                 125

Pro Leu Ser Glu Gly Arg Ile Asp Gln Trp Gly Arg Leu Gln Cys Val
        130                 135                 140

Tyr His Gly Trp Cys Phe Asp Gly Val Gly Ala Cys Lys Phe Ile Pro
145                 150                 155                 160

Gln Ala Pro His Asp Gly Pro Val Glu Thr Ser Lys Lys Ala Cys
                165                 170                 175

Val Lys Gly Val Tyr Pro Ser Cys Val Arg Asn Gly Ile Val Trp Phe
            180                 185                 190

Trp Pro Asn Ser Asp Pro Lys Tyr Lys Asp Ile Tyr Leu Thr Asn Lys
        195                 200                 205
```

Pro His Tyr Ile Pro Glu Leu Asp Asp Pro Ser Phe Thr Cys Thr Thr
    210                 215                 220

Ile Thr Arg Glu Val Pro Tyr Gly Tyr Glu Ile Leu Ala Glu Asn Leu
225                 230                 235                 240

Met Asp Pro Ser His Val Pro Tyr Ala His Tyr Gly Ile Leu Glu Leu
                245                 250                 255

Glu Lys Val Lys Glu Ser Ser Lys Arg Asp Arg Glu Gly Gly His Glu
            260                 265                 270

Met Glu Ile Ser Val Gly Thr Ile Asp Val Asn Gly Phe Ser Ala Lys
        275                 280                 285

His Val Ser Ala Asp Tyr Tyr Phe Val Pro Pro Tyr Val Tyr Tyr Gly
    290                 295                 300

Arg Ile Thr Pro Asn Ala Ala Thr Lys Thr Lys Asp Ala Thr Leu Pro
305                 310                 315                 320

Val Val Pro Glu Glu Lys Thr Ala Met Ile Val Phe Tyr Cys Ile Pro
                325                 330                 335

Val Thr Pro Gly Tyr Ser Arg Leu Ile Tyr Ala Gly Ala Arg Asn Phe
            340                 345                 350

Ala Val Gln Ile Asp Arg Phe Val Pro Arg Trp Ile Thr His Met Ser
        355                 360                 365

His Asn Leu Ile Phe Asp Ser Asp Leu Phe Leu His Val Glu Glu
    370                 375                 380

Gln Lys Leu Lys Asp Leu Asp Trp His Lys Ser Cys Tyr Ile Pro Thr
385                 390                 395                 400

Lys Ala Asp Gly Gln Val Val Ala Phe Arg Arg Trp Leu Asn Lys Tyr
                405                 410                 415

Gly Gly Thr Gln Val Asp Trp Arg Asn Asn Phe Thr Pro Ala Leu Pro
            420                 425                 430

Pro Thr Pro Ser Arg Glu Gln Leu Phe Asp Arg Tyr Trp Ser His Thr
        435                 440                 445

Ala Glu Cys Ser Ser Cys Ser Val Ala Cys Lys Arg Leu Asn Ala Leu
    450                 455                 460

Glu Ile Gly Leu Gln Ala Met Ser Leu Val Phe Val Ala Met Ala Ala
465                 470                 475                 480

Ala Val Ser Ala Pro Ala Thr Arg Tyr Ser Met Val Ala Met Ala Val
                485                 490                 495

Leu Ser Phe Leu Ala Ser Lys Trp Leu Ser His Phe Ile His Lys Thr
            500                 505                 510

Phe Tyr Asn His Gly Tyr Asp His Ala Phe Val
        515                 520

<210> SEQ ID NO 8
<211> LENGTH: 151
<212> TYPE: PRT
<213> ORGANISM: Ocimum basilicum

<400> SEQUENCE: 8

Met Ala Thr Thr Gln Leu Pro Ser Asn Thr Ala Ile Lys Ser Ala Leu
1               5                   10                  15

Gln Asn Gln Ile Ala Ser Pro Phe Val Lys Leu Pro Val Ser Leu Gly
            20                  25                  30

Ser Val Lys Arg Ala Thr Lys Ala Phe Gly Leu Thr Ala Lys Pro Asn
        35                  40                  45

Phe Arg Ala Ser Ala Met Ala Thr Tyr Lys Val Lys Leu Ile Gly Pro

```
                50                  55                  60
Asp Gly Glu Glu Ser Glu Phe Glu Ala Pro Asp Asp Cys Tyr Ile Leu
 65                  70                  75                  80

Asp Ser Ala Glu Ala Ala Gly Val Glu Leu Pro Tyr Ser Cys Arg Ala
                 85                  90                  95

Gly Ala Cys Ser Thr Cys Ala Gly Lys Val Ala Ser Gly Ser Val Asp
                100                 105                 110

Gln Ser Asp Gly Ser Phe Leu Asp Glu Lys Gln Met Glu Glu Gly Tyr
            115                 120                 125

Leu Leu Thr Cys Val Ser Tyr Pro Thr Ala Asp Cys Val Ile His Thr
            130                 135                 140

His Lys Glu Ser Asp Leu Tyr
145                 150

<210> SEQ ID NO 9
<211> LENGTH: 372
<212> TYPE: PRT
<213> ORGANISM: Ocimum basilicum

<400> SEQUENCE: 9

Leu Ala Gln Val Pro Val Ala Val Ser Val Lys Asn Asp Val Ser Leu
 1               5                  10                  15

Arg Ser Ser Val Phe Lys Ser Asn Asn Val Ser Phe His Glu Thr Ser
                20                  25                  30

Arg Ala Ser Arg Leu Ser Met Asp Phe Arg Ala Thr Ser Phe Lys Ser
             35                  40                  45

Arg Ser Gln Pro Val Val Cys Met Ser Val Gln Gln Ala Ser Lys Ser
 50                  55                  60

Lys Val Ala Val Ser Pro Leu Ser Leu Glu Asp Ala Lys Asp Pro Pro
 65                  70                  75                  80

Leu His Leu Phe Lys Asn Lys Glu Pro Tyr Glu Gly Thr Ile Val Ser
                 85                  90                  95

Val Glu Arg Leu Val Gly Pro Gln Ala Pro Gly Glu Thr Cys His Ile
                100                 105                 110

Val Ile Asp His Gly Gly Lys Val Pro Tyr Trp Glu Gly Gln Ser Tyr
            115                 120                 125

Gly Ile Ile Pro Pro Gly Glu Asn Pro Lys Lys Pro Gly Asn Pro His
130                 135                 140

Asn Val Arg Leu Tyr Ser Ile Ala Ser Thr Arg Tyr Gly Asp Ser Phe
145                 150                 155                 160

Asp Gly Lys Thr Ala Ser Phe Cys Val Arg Arg Ala Val Tyr Tyr Asp
                165                 170                 175

Pro Glu Thr Gly Lys Glu Asp Pro Ser Lys Gly Val Cys Ser Asn
                180                 185                 190

Phe Leu Cys Asp Ser Lys Pro Gly Asp Lys Val Gln Ile Thr Gly Pro
            195                 200                 205

Ser Gly Lys Ile Met Leu Leu Pro Glu Asp Pro Lys Ala Thr His
210                 215                 220

Ile Met Ile Ala Thr Gly Thr Gly Val Ala Pro Phe Arg Gly Tyr Leu
225                 230                 235                 240

Arg Arg Met Phe Met Glu Asp Val Pro Thr Phe Lys Phe Asn Gly Leu
                245                 250                 255

Ala Trp Leu Phe Leu Gly Val Ala Asn Lys Asp Ser Leu Leu Tyr Asp
            260                 265                 270
```

```
Asp Glu Phe Ser Lys Tyr Leu Gln Asp Tyr Pro Asp Asn Phe Arg Phe
            275                 280                 285

Asp Arg Ala Leu Ser Arg Glu Gln Lys Asn Arg Asn Gly Gly Lys Met
    290                 295                 300

Tyr Val Gln Asp Lys Ile Glu Glu Tyr Ser Asp Glu Val Phe Lys Leu
305                 310                 315                 320

Leu Asp Asn Gly Ala His Ile Tyr Phe Cys Gly Leu Lys Gly Met Met
                325                 330                 335

Pro Gly Ile Gln Asp Thr Leu Lys Lys Val Ala Glu Gln Arg Gly Glu
            340                 345                 350

Asn Trp Glu Glu Lys Leu Ser Gln Leu Lys Lys Asn Lys Gln Trp His
            355                 360                 365

Val Glu Val Tyr
    370

<210> SEQ ID NO 10
<211> LENGTH: 28
<212> TYPE: DNA
<213> ORGANISM: Artificial Sequence
<220> FEATURE:
<223> OTHER INFORMATION: Synthetic primer

<400> SEQUENCE: 10
atactagtat ggggcgggac gaagaggc                                           28

<210> SEQ ID NO 11
<211> LENGTH: 32
<212> TYPE: DNA
<213> ORGANISM: Artificial Sequence
<220> FEATURE:
<223> OTHER INFORMATION: Synthetic primer

<400> SEQUENCE: 11
atcatcgatt cagggataag cctcaatgag tg                                      32

<210> SEQ ID NO 12
<211> LENGTH: 37
<212> TYPE: DNA
<213> ORGANISM: Artificial Sequence
<220> FEATURE:
<223> OTHER INFORMATION: Synthetic primer

<400> SEQUENCE: 12
actagtatgg gaattcatct cgtttgtcta caccctc                                 37

<210> SEQ ID NO 13
<211> LENGTH: 40
<212> TYPE: DNA
<213> ORGANISM: Artificial Sequence
<220> FEATURE:
<223> OTHER INFORMATION: Synthetic primer

<400> SEQUENCE: 13
atcatcgatt caataaatct caacgatctc attatagagt                              40

<210> SEQ ID NO 14
<211> LENGTH: 31
<212> TYPE: DNA
<213> ORGANISM: Artificial Sequence
<220> FEATURE:
<223> OTHER INFORMATION: Synthetic primer

<400> SEQUENCE: 14
```

```
atactagtat ggcggtagac aaagaagttg a                              31

<210> SEQ ID NO 15
<211> LENGTH: 32
<212> TYPE: DNA
<213> ORGANISM: Artificial Sequence
<220> FEATURE:
<223> OTHER INFORMATION: Synthetic primer

<400> SEQUENCE: 15
atcatcgatt caaggataag cctcaattac aa                             32

<210> SEQ ID NO 16
<211> LENGTH: 33
<212> TYPE: DNA
<213> ORGANISM: Artificial Sequence
<220> FEATURE:
<223> OTHER INFORMATION: Synthetic primer

<400> SEQUENCE: 16
actagtatgg tggcagacga agaagcccaa ctt                            33

<210> SEQ ID NO 17
<211> LENGTH: 33
<212> TYPE: DNA
<213> ORGANISM: Artificial Sequence
<220> FEATURE:
<223> OTHER INFORMATION: Synthetic primer

<400> SEQUENCE: 17
atcgattcaa ggataggcct caatcacaaa ctc                            33

<210> SEQ ID NO 18
<211> LENGTH: 30
<212> TYPE: DNA
<213> ORGANISM: Artificial Sequence
<220> FEATURE:
<223> OTHER INFORMATION: Synthetic primer

<400> SEQUENCE: 18
actagtatgg cggtagacaa agaagttcaa                                30

<210> SEQ ID NO 19
<211> LENGTH: 33
<212> TYPE: DNA
<213> ORGANISM: Artificial Sequence
<220> FEATURE:
<223> OTHER INFORMATION: Synthetic primer

<400> SEQUENCE: 19
atcgattcaa ggataggcct caatcacgga ctc                            33

<210> SEQ ID NO 20
<211> LENGTH: 95
<212> TYPE: DNA
<213> ORGANISM: Artificial Sequence
<220> FEATURE:
<223> OTHER INFORMATION: Synthetic primer

<400> SEQUENCE: 20
ggatccatgt tgttctataa gcctgtgatg aggatggcgg tgagaccgct aaaaagcata    60
agattccagg ccgcgactac tccgactgtc gcgtg                              95

<210> SEQ ID NO 21
<211> LENGTH: 33
```

```
<212> TYPE: DNA
<213> ORGANISM: Artificial Sequence
<220> FEATURE:
<223> OTHER INFORMATION: Synthetic primer

<400> SEQUENCE: 21
ggatcctcag acaaaggcat gatcataacc atg                          33

<210> SEQ ID NO 22
<211> LENGTH: 97
<212> TYPE: DNA
<213> ORGANISM: Artificial Sequence
<220> FEATURE:
<223> OTHER INFORMATION: Synthetic primer

<400> SEQUENCE: 22
gcggccgcat gttgttctat aagcctgtga tgaggatggc ggtgagaccg ctaaaaagca    60
taagattcca gtcctcagca atggcaacat acaaggt                            97

<210> SEQ ID NO 23
<211> LENGTH: 34
<212> TYPE: DNA
<213> ORGANISM: Artificial Sequence
<220> FEATURE:
<223> OTHER INFORMATION: Synthetic primer

<400> SEQUENCE: 23
actagtctaa tacaaatcac tctccttgtg agtg                         34

<210> SEQ ID NO 24
<211> LENGTH: 95
<212> TYPE: DNA
<213> ORGANISM: Artificial Sequence
<220> FEATURE:
<223> OTHER INFORMATION: Synthetic primer

<400> SEQUENCE: 24
ggatccatgt tgttctataa gcctgtgatg aggatggcgg tgagaccgct aaaaagcata    60
agattccagt cctccgtgca acaagccagc aaatc                              95

<210> SEQ ID NO 25
<211> LENGTH: 33
<212> TYPE: DNA
<213> ORGANISM: Artificial Sequence
<220> FEATURE:
<223> OTHER INFORMATION: Synthetic primer

<400> SEQUENCE: 25
ggatcctcag taaacctcaa catgccattg ttt                          33

<210> SEQ ID NO 26
<211> LENGTH: 32
<212> TYPE: DNA
<213> ORGANISM: Artificial Sequence
<220> FEATURE:
<223> OTHER INFORMATION: Synthetic primer

<400> SEQUENCE: 26
ctcgagatgc catcatccag tggagtagat tc                           32

<210> SEQ ID NO 27
<211> LENGTH: 30
<212> TYPE: DNA
<213> ORGANISM: Artificial Sequence
<220> FEATURE:
```

<223> OTHER INFORMATION: Synthetic primer

<400> SEQUENCE: 27
ggtaccctag gggaaaactt caattaaaga                30

PRODUCTION OF HYDROXYLATED AND METHOXYLATED FLAVONOIDS IN YEAST BY EXPRESSION SPECIFIC ENZYMES

STATEMENT OF FEDERALLY SPONSORED RESEARCH AND DEVELOPMENT

This invention was made with government support under contract number DE-SC001728 awarded by the United States Department of Energy. The United States government has certain rights in the invention.

BIOLOGICAL DEPOSIT

Biological recombinant yeast strains SALV-1, 8HS-1, GB-1, CIRM-1 and LAD-1 have been deposited on Apr. 2, 2019 under the Budapest Treaty as Accession Nos. NRRL Y-67759, NRRL Y-67760, NRRL Y-67761, NRRL Y-67762 and NRRL Y-67763, respectively, on Apr. 4, 2019, with the Agricultural Research Service Culture Collection Northern Regional Research Laboratory (NRRL), in Peoria, Ill., with the following mailing address ARS Culture Collection (NRRL), 1815 N. University Street, Peoria, Ill. 61604.

SEQUENCE LISTING

This application includes as the Sequence Listing the complete contents of the accompanying text file "Sequence.txt", created Apr. 25, 2019, containing 65,536 bytes, hereby incorporated by reference.

BACKGROUND OF THE INVENTION

Field of the Invention

The invention generally relates to recombinant yeast strains that produce methoxylated and/or hydroxylated flavonoids. In particular, the invention provides recombinant yeast strains that are genetically modified to contain and express one or more plant genes or gene pathways (e.g. a hydroxylase and a methyltransferase) that produce methoxylated and/or hydroxylated flavones and flavonols.

Description of Related Art

Efforts to engineer flavonoid metabolism in microorganisms have been conducted for over a decade. Among the target modifications and molecules, the production of lipophilic (poly)methoxylated flavonoids has not been extensively addressed. These compounds occur in numerous land plant families and often possess pronounced bioactivities. Ready access to larger quantities of pure (poly)methoxylated flavonoids would facilitate a better assessment of their pharmacological potential as well as the generation of novel chemical entities.

The structural diversity of (poly)methoxylated flavonoids depends on "decorative" hydroxylations of their backbone (see the apigenin structure presented in FIG. 1). Most frequently, positions 3' and 5' of ring B and 6 and 8 of ring A carry such decorative hydroxyl groups that can be subsequently methylated.

There is a need in the art to provide additional means of producing modified flavonoids.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Numerous methoxylated flavonoids that exhibit pronounced bioactivities are produced by plants and their biotechnological production and diversification are of great interest to pharmaceutical and nutraceutical industries. However, the amounts produced by plants are insufficient to meet the growing demand. The present disclosure addresses this unmet need by providing yeast that are genetically modified to produce hydroxylated and/or methoxylated flavonoids. As an example, a set of enzymes from sweet basil (*Ocimum basilicum*) was used to construct strains of *Saccharomyces cerevisiae* which produce 8- and/or 6-substituted, methoxylated flavones from a natural precursor (apigenin). Growth parameters affecting the overall yields and flux were identified, permitting optimization of conditions for production. In addition, the ability of the engineered strains to utilize alternative substrates was also determined. The yeast cells produced substantial amounts of 6-hydroxylated, methylated derivatives of naringenin and luteolin and the corresponding derivatives of the flavonol kaempferol were detected, in addition to other products and intermediates.

It is an object of this disclosure to provide a recombinant yeast that has been transformed with at least one heterologous plant gene encoding a flavonoid ring A hydroxylase; and at least one heterologous plant gene encoding a flavonoid O-methyltransferase. In some aspects, the flavonoid O-methyltransferase is a flavonoid 7-O-methyltransferase (F7OMT) and the flavonoid ring A hydroxylase is a flavonoid 6-hydroxylase (F6H). Those of skill in the art will recognize that the F6H works on (hydroxylates) 7-O-methylated flavonoids; thus the activity of an F7OMT is typically required before a 6-OH residue is introduced by an F6H. In additional aspects, the F7OMT is ObFOMT1. In some aspect, the F6H is ObF6H-1. In some aspects, the recombinant yeast is also transformed with at least one heterologous plant gene encoding one or more of: a flavonoid 4-O-methyl transferase (F4OMT); a flavonoid 5-O-methyl transferase (F5OMT); a flavonoid 6-O-methyl transferase (F6OMT); a flavonoid 8-O-methyltransferase (F8OMT); a bifunctional enzyme with both flavonoid 4-O-methyl transferase and 6-O-methyl transferase activity; or a flavone 8-hydroxylase (F8H). In further aspects, the bifunctional enzyme is ObFOMT3. In additional aspects, the at least one heterologous gene encodes a flavone 8-hydroxylase (F8H) and the recombinant yeast is further transformed with a heterologous gene encoding an Fdx-NADP$^+$ reductase. In other aspects, the at least one heterologous plant gene encoding a flavonoid ring A hydroxylase and the at least one heterologous plant gene encoding at least one flavonoid O-methyltransferase are from sweet basil (*Ocimum basilicum*). In additional aspects, the recombinant yeast is a recombinant *Saccharomyces cerevisiae*. In yet further additional aspects, the recombinant yeast is selected from the group consisting of:

SALV-1 deposited with NRRL under deposit number NRRL Y-67759;

8HS-1 deposited with NRRL under deposit number NRRL Y-67760;

GB-1 deposited with NRRL under deposit number NRRL Y-67761;

CIRM-1 deposited with NRRL under deposit number NRRL Y-67762; and

LAD-1 deposited with NRRL under deposit number NRRL Y-67763.

Also provided is a method for producing at least one hydroxylated flavonoid and/or at least one methoxylated flavonoid, comprising i) culturing the recombinant yeast of claim 1 with at least one precursor of either or both the at least one hydroxylated flavonoid and/or the at least one methoxylated flavonoid, wherein the step of culturing is performed under conditions suitable to produce the at least one hydroxylated flavonoid and/or methoxylated flavonoid; and ii) recovering the at least one hydroxylated and/or the at least one methoxylated flavonoid produced during culturing. In some aspects, the at least one precursor is apigenin (API), naringenin (NAR), luteolin (LUT) or kaempferol (KAEM). In further aspects, the at least one hydroxylated flavonoid and/or methoxylated flavonoid is: i) scutellarein-7-methyl ether, cirismaritin, ladanein, salvigenin, 8-hydroxysalvigenin, gardenin B and/or genkwanin if API is fed; ii) 2,3-dihydro-cirsimaritin, 2,3,-dihydro-ladanein, sakuranetin and/or carthamidin-7-methylether if naringenin is fed; iii) pedalitin, cirsiliol, L7Me and/or eupatorine if luteolin is fed; and iv. one or more 7-methyl- and/or 7,4'-dimethylated derivatives when kaempferol is fed. In additional aspects, the at least one heterologous plant gene encoding a flavonoid ring A hydroxylase and the at least one heterologous plant gene encoding at least one flavonoid O-methyltransferase are from sweet basil (*Ocimum basilicum*). In some aspects, the recombinant yeast is a recombinant *Saccharomyces cerevisiae*. In other aspects, the recombinant yeast is selected from the group consisting of:

SALV-1 deposited with NRRL under deposit number NRRL Y-67759;

8HS-1 deposited with NRRL under deposit number NRRL Y-67760;

GB-1 deposited with NRRL under deposit number NRRL Y-67761;

CIRM-1 deposited with NRRL under deposit number NRRL Y-67762; and

LAD-1 deposited with NRRL under deposit number NRRL Y-67763.

BRIEF DESCRIPTION OF THE DRAWINGS

FIGS. 1A and B. A, steps of flavone biosynthesis in sweet basil used for flavonoid production by constructed yeast strains. Bold arrows indicate major pathways, thinner arrows indicate side reactions; B, structures of flavonoids offered as alternative substrates in this study. Flavonoid backbone nomenclature is shown on the structure of apigenin.

FIG. 2. Biofermentation products of apigenin with five constructed strains. $UV_{335}$ traces of bioconversion products extracted from the whole cell suspension after two days of growth in shake flasks/rich medium. Strains are indicated in the upper right corner of each trace. IS: internal standard quercetagetin. Other compound abbreviations as in text. Vertical dotted lines connect the same compounds across strains.

FIG. 16A-H. Chromatograms and mass spectra of 6-hydroxylated biofermentation products with kaempferol as fed substrate. A-C, selected ion chromatograms. The strains and height of largest peak are indicated in the upper right corner, the ion monitored in the left upper corner; D-H, predicted and observed isotope models and accurate masses of the peaks shown in A-C. Metabolites shown, formulae and mass errors are indicated in the upper right corner.

DETAILED DESCRIPTION

Definitions

Figure 3A:
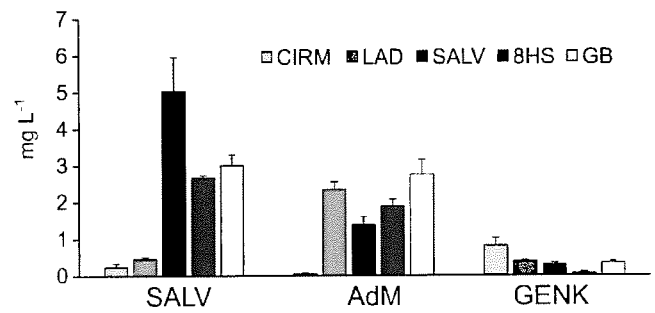
FIGS. 3A and B. Flavone production under different fermentation conditions. A, abundance of SALV, AdM and GENK; B, abundance of s7Me and LAD. Legend indicates yeast strain. Error bars represent standard deviation (n=3).

Flavonoids (or bioflavonoids) are a class of plant and fungus secondary metabolites. Chemically, flavonoids have the general structure of a 15-carbon skeleton, which consists of two phenyl rings (A and B) and a heterocyclic ring (C) between rings A and B (see FIG. 1). This carbon structure can be abbreviated C6-C3-C6.

Plant O-methyltransferases (OMTs) are enzymes that methylate oxygen atoms of a variety of secondary metabolites including phenylpropanoids, flavonoids, and alkaloids.

Hydroxylases are enzymes that catalyze the formation of hydroxyl groups by oxidation of a substrate.

Substrate: the material or substance on which an enzyme acts. Herein "substrate" may be used interchangeably with "precursor". As used herein, an enzyme substrate can be a precursor of an intermediate in a biosynthetic pathway or the immediate precursor of the end-product of the biosynthetic pathway. In addition, because multi-step pathways are described, a "substrate" or "precursor" may also be referred to as a "product" of one step of the pathway, and/or a product of one step of a pathway may be used as a substrate (precursor) for one or more steps that follow in the pathway.

The pathways described herein are biosynthetic pathways, i.e. they are multi-step, enzyme-catalyzed processes where substrates are converted into other compounds. The pathways may be linear or branched, and the discussion herein may refer to an entire pathway (from initial substrate to final product) or a portion or segment of the pathway (e.g. from a substrate to an intermediate).

Enzyme nomenclature: enzyme nomenclature such as "ObF8H-1" and "ObF8H1", etc. (i.e. with and without a hyphen) refer to the same enzyme.

Abbreviations

AdM: apigenin-7, 4'-dimethyl ether
API: apigenin
CIRL: cirsiliol (3'-OH-CIRM)
CIRM: cirismaritin, which is 6,7-dimethylated scutellarei; "CIRM" is also used as a designation for a strain described herein
EUP: eupatorin
GB: gardenin B; "GB" is also used as a designation for a strain described herein
GENK: genkwanin
8HS: 8-hydroxysalvigenin; "8HS" is also used as a designation for a strain described herein
KAEM: kaempferol
L7Me: 7-methylluteolin (L7Me)
LAD: ladanein; "LAD" is also used as a designation for a strain described herein
LdM: Luteolin-7,4'-dimethyl ether by analogy to 7-methylluteolin above)
LUT: luteolin
NAR: naringenin
NUCH: nuchensin
PED: Pedalitin (6-hydroxy-L7Me)
SALV: trimethylated salvigenin; "SALV" is also used as a designation for a strain described herein
S7Me: scutellarein-7-methyl ether
FOMT: flavonoid-O-methyltransferase
FH: flavonoid hydroxylase

Yeast

The present disclosure describes genetically engineered/modified yeast cells. The yeast cells may belong to the genus *Saccharomyces*, *Kluyveromyces*, *Candida*, *Pichia*, *Issatchenkia*, *Debaryomyces*, *Zygosaccharomyces*, *Shizosaccharomyces*, or *Saccharomycopsis*. In some aspects, the yeast genus is *Saccharomyces* is, for example, *Saccharomyces cerevisiae* (*S. cerevisiae*), *Saccharomyces bayanus* (*S. bayanus*), *Saccharomyces boulardii* (*S. boulardii*), *Saccharomyces bulderi* (*S. bulderi*), *Saccharomyces cariocanus* (*S. cariocanus*), *Saccharomyces cariocus* (*S. cariocus*), *Saccharomyces chevalieri* (*S. chevalieri*), *Saccharomyces dairenensis* (*S. dairenensis*), *Saccharomyces ellipsoideus* (*S. ellipsoideus*), *Saccharomyces eubayanus* (*S. eubayanus*), *Saccharomyces exiguus* (*S. exiguus*), *Saccharomyces florentinus* (*S. florentinus*), *Saccharomyces kluyveri* (*S. kluyveri*), *Saccharomyces martiniae* (*S. martiniae*), *Saccharomyces monacensis* (*S. monacensis*), *Saccharomyces norbensis* (*S. norbensis*), *Saccharomyces paradoxus* (*S. paradoxus*), *Saccharomyces pastorianus* (*S. pastorianus*), *Saccharomyces spencerorum* (*S. spencerorum*), *Saccharomyces turicensis* (*S. turicensis*), *Saccharomyces unisporus* (*S. unisporus*), *Saccharomyces uvarum* (*S. uvarum*), or *Saccharomyces zonatus* (*S. zonatus*). In some aspects, the yeast is a *S. cerevisiae* yeast.

Other types of yeast that may be used include but are not limited to: *Schizosaccharomyces pombe* ("fission yeast"), *Pichia pastoris*, etc.

In addition, the yeast that are used may already be genetically modified prior to their use as described. For example, the yeast may be modified for use in various expression systems or systems which allow the detection of transformants e.g. by amino acid or nucleotide complementation; blue-white screening methods; the URA3 method (which relies on growth on Yeast Synthetic Drop-out Medium Supplements without uracil); adenine method; fluorescent markers such as YOYO-1; etc.

Genes

Generally, the genes or gene pathways that are inserted into a yeast are involved in and/or responsible for the production of hydroxylated and/or methoxylated flavonoids from suitable precursors. The genes are derived from or obtained from plants, i.e. in nature, they occur in plants.

Types of plants that contain genes that can be successfully transferred to yeast include but are not limited to: basil plants, for example, a species of the genus *Ocimum* such as *O. basilicum* (sweet basil) or cultivars, varieties and hybrids thereof. These include but at not limited to: *O. basilicum* 'Lettuce Leaf'; *O. basilicum* 'Mammoth'; *O. basilicum* 'Genovese Gigante'; *O. basilicum* 'Nufar F1'; *O. basilicum* 'Spicy Globe'; *O. basilicum* 'Greek Yevani'; *O. basilicum* piccolo; *O. basilicum* 'Boxwood'; *O. basilicum* 'Purple Ruffles'; *O. basilicum* 'Magical Michael'; *O. basilicum* 'Purpurascens'; *O. basilicum* 'Red Rubin'; *O. basilicum* 'Osmin Purple'; *O. basilicum* var. *thyrsiflorum* 'Siam Queen'; *O. basilicum* var. *thyrsiflorum*; *O. basilicum* 'Cinnamon'; *O. basilicum* 'Licorice'; *O. basilicum* var. *citriodora* 'Mrs. Burns'; or *Ocimum americanum* (formerly known as *O. canum*) cultivars such as lemon and lime basil; or *Ocimum×citriodorum* cultivars such as *O.×citriodorum* 'Lesbos'; *O.×citriodorum*; and other species and hybrids e.g. *O. sanctum; O. gratissimum; O. minimum; O. kilimandscharicum×basilicum; O. basilicum×americanum; O. basilicum×americanum*, etc.

In some aspects, the type of plant that is the source of the genes is basil. However, this is not the only example of a suitable plant. Similar compounds occur in numerous members of the Lamiaceae family, for example, in species of the genus *Mentha* (including *Mentha×piperita* and others (e.g. F6H from *M. piperita*) and species of the genus *Salvia* and genes from these exemplary sources may also be employed.

In other aspects, the genes may or may not be sourced from (originate from) e.g. a *Petunia* species (e.g. *Petunia hybrida*) or an *Arabidopsis* species such as *Arabidopsis thaliana*. In further aspects, the gene is or is not sourced from (originates from): a *Medicago* species such as *Medicago sativa*; a *Pueraria* species such as *Pueraria lobate*; or a *Petroselinum* (parsley) species such as *Petroselinum crispus*; soybean, *Catharanthus roseus*, snapdragon, *Malta domestica*, *Lilium hybrida*, carrot, *Ipomoea purpurea*, *Ipomoea nil*, *Anthurium andraeanum*, strawberry, *Rosa hybrida*, *Dianthus gratianopolitanus* or *Desmodium uncinatum*.

Enzymes and Pathways

The recombinant yeasts that are disclosed herein are genetically modified to include heterologous (i.e. non-yeast) genes that encode enzymes that participate in pathways that produce one or more flavonoids of interest, and/or that produce one or more intermediates of one or more pathways that produce at least one flavonoid of interest. The enzymes may be regioselective or permissive.

As an example, if a pathway to produce exemplary Flavonoid X is a multistep pathway having 3 synthetic steps that are catalyzed by 3 enzymes, then the first enzyme converts the initial substrate to a first intermediate, a second enzyme converts the first intermediate into a second intermediate, and the third enzyme converts the second intermediate into the final product, Flavonoid X, i.e. two intermediates are formed in the pathway. Herein, recombinant yeasts or systems of recombinant yeasts are disclosed which can perform i) an entire pathway to produce a desired flavonoid, or ii) one or more steps of (i.e. a segment of) the pathway to produce an intermediate that is passed e.g. as a "substrate", to another organism (such as another recombinant yeast) that is capable of performing one or more (e.g. all) of the remaining steps of the pathway. (Alternatively, the intermediate may be used as an enzyme substrate in an extracellular enzyme synthetic system.)

Accordingly, in a first aspect, one yeast strain is engineered to contain and express all of the enzymes in a pathway of interest, and in a second aspect, one yeast strain is engineered to contain and express at least one of the enzymes in the pathway. In the second aspect, the yeast strain may be, for example, co-cultured with other strains which perform the other synthesis steps; or the intermediate produced by the yeast strain may be retrieved (e.g. isolated) and used as a substrate for another organism (or other organisms or cells in culture, e.g. yeast, bacteria, culture plant cells, etc.) which perform the remaining synthesis steps. Alternatively, the "intermediates" described herein may be beneficial in and of themselves, and are thus isolated and used for purposes other than as substrates, e.g. useful purposes that do not involve the other steps of the pathway.

The genes that make up the gene pathways and/or segments of gene pathways described herein and that may be used to genetically modify the yeasts include but are not limited to:

1. Methyltransferases, in particular flavonoid O-methyltransferases (FOMTs), including but not limited to:

a flavonoid 4-O-methyl transferase (F4'OMT) such as the basil enzyme ObFOMT5, an enzyme whose preferred substrate is S7Me and which is strongly selective for the 4'-OH moiety as acceptor; this enzyme also shows some F6OMT activity with the substrate LAD;

a flavonoid 6-O-methyltransferase (F6OMT) such as the basil enzyme ObFOMT4, which catalyzes the 6-O-methylation of e.g. S7Me;

a flavonoid 8-O-methyltransferase (F8OMT) such as the basil enzyme, ObF8OMT1, this enzyme converts OH at position 8 of a flavonoid ring to $OCH_3$;

a bifunctional flavonoid 4'-O-methyl transferase/6-O-methyl transferase such as the basil enzyme, ObFOMT3. This enzyme acts primarily as an F4'OMT (e.g. with the substrate S7Me in planta) and also has significant 6-O-methylating activity (F6'OMT activity e.g. with the substrate LAD in planta);

ObFOMT1, which is a flavonoid 7-O-methyltransferase.

2. Hydroxylases, in particular plant hydroxylases, which include but are not limited to:

CYP82D33: a flavone 6-hydroxylase (F6H), such as the F6H from basil (ObF6H-1);

CYP82D62: a flavone 6-hydroxylase (F6H) from peppermint; a flavone 8-hydroxylase (F8H) such as the F8H of basil (ObF8H-1, basil flavone 8-hydroxylase), a Rieske-type oxygenase. This enzyme requires reduced ferredoxin (Fdx) as an electron donor, and thus typically Fdx-$NADP^+$ reductase (FNR) is also expressed in the same organism, etc.

In some aspects, the enzyme is or is not a tyrosine ammonia lyase (TAL), a 4-coumarate:CoA ligase (4CL), a chalcone synthase (CHS), and/or a chalcone isomerase (CHI).

In further aspects, the enzyme is or is not a coumarate 4-hydroxylase (C4H), a 4-coumaroyl-CoA ligase (4CL), a Chalcone synthase (CHS), a Chalcone isomerase (CHI), a Flavonoid 3'5' hydroxylase (F3'5'H), a Flavanone 3-hydroxylase (FHT), a Dihydroflavonol 4-reductase (DFR), an Anthocyanidin synthase (ANS), or a UDP-glucose:flavonoid 3-O-glucosyltransferase (3-GT); or a set of genes encoding for C4H, 4CL, CHS and CHI; C4H, 4CL, CHS, CHI, F3H, FHT, DFR and Leucoanthocyanidin reductase (LAR); C4H, 4CL, CHS, CHI, F3H, FHT and flavonol synthase (FLS); C4H, 4CL, CHS, CHI, F3H, FHT, DFR and ANS; or C4H, 4CL, CHS, CHI and Flavone Synthase I (FSI) or Flavone Synthase II (FSII); or FHT, F3'S'H, DFR, ANS and 3-GT.

Enzyme Combinations

In some aspects, the recombinant yeasts include both an F7OMT (e.g. basil ObFOMT1) and an F6H (e.g. the basil flavonoid 6-hydroxylase (F6H) encoded by CYP82D33 (ObF6H-1).

In additional aspects, the recombinant yeasts include e.g. both ObFOMT1 and ObF6H-1 plus one or more additional enzymes, such as:
  an enzyme with F4'OMT activity (e.g. basil ObFOMT5)
  an enzyme with F7OMT activity (e.g. basil ObFOMT1)
  an enzyme with F6OMT activity (e.g. basil ObFOMT4),
  a permissive, bifunctional enzyme such as basil ObFOMT3, which has both flavonoid 4'-O-methyl transferase and flavonoid 6-O-methyl transferase activity,
  an enzyme with F8H activity (e.g. basil ObF8H-1), and, if an enzyme with F8H activity is included, then an enzyme with Fdx-NADP+ reductase activity.

Enzyme Sequences

Exemplary amino acid sequences of exemplary plant enzymes that are encoded by the recombinant yeast described herein are as follows:

```
ObFOMT1 (AFU50295.1 flavonoid O-methyltransferase 1
[Ocimum basilicum])
                                       (SEQ ID NO: 1)
MGRDEEAAAQAEAWNHGFGFIKTSVIKTAIELEIPDILHNQGGPLSLSAL

SSAVGVPPDRLHRIMRFLAHHGVSKKTASPPGESDYYYAETAVSRSLTKD

NLGPFVLLQGAQRGPSACITAQGLKSRERPGVEELGSDPLYEDPIFTEKV

FRDAMTCHARVTTSAVIENYGEGFRGVGSLVDVGGSYGMTLGMLVEAFPW

IRGICYDLPPVVAKAKPLHGVEFVAGSMFESVPKADVIMLMFVLHNWSDN

ECIDILKRCKEAIPAETGRLMIIDAIIDEDGEGDEFAGARLGLDVTMMAV

TYEGKERTHREWAYILTEAGFRKYVVNNIKALESLIEAYP;

ObFOMT3 (AFU50297.1 flavonoid O-methyltransferase 3
[Ocimum basilicum])
                                       (SEQ ID NO: 2)
MAVDKEVQLHAQAWEHALSYINSTALSAAVELEIPDILEDHGGLMSLSEL

SAASGCPREPLYRLMRFLIFHGIFTKSDDCYAQSPLSRLFTRENLGPYML

MQATPVTRSPAGLSGEALKTGTSLYLKSIRGEDSWSDPAYGYHMKAFTNA

MIAHARLTAAAIVSNYPAAFDGLRSVVDVGGRHGTAIGRLVEAFPWVRGI

AFDLPEIVADAPPRKGVDFVGGDMFESVPKADAVMLMWILHDWSDDKCIE

ILKKCKEAIPASTGKVMIVDAIINEDGEGDEFSGARLSLDMIMLAVMAQG

KERTYKEWVHLLNEAGFSKHTVKNIKSIESVIEAYP;

ObFOMT4 (AFU50298.1 flavonoid O-methyltransferase
4 [Ocimum basilicum])
                                       (SEQ ID NO: 3)
MAVDKEVELHAQAWDHALSYITPTALSAAVELEIPDILEDHGGLMSLSEL

SAASGCPREPLYRLMRFLIFHGIFTKSNDCYAQSPLSRVFTRENLGPYML

MQATPVTRSPAGLSGEALKTGTPLYLKSIRGEDSWNDPAYGFHMRAFTNG

MAAHARLTAAAIVTNYPTAFNGVRSVVDVGGRHGMAIGKLVEAFPWVRGI

AFDLPEVVADAPPRKGVDFVGGDMFESLPKADAVMLMWVLHDWSDDKCIE

ILKKCKEAIPTSTGKVMIVDAIINEEGEGDEFSGARLSLDMTMMAMTTQG

KERSYKEWVHLLNEAGFSKHTVKNIKTIEFVIEAYP;

ObFOMT5 (AFU50299.1 flavonoid O-methyltransferase
5 [Ocimum basilicum])
                                       (SEQ ID NO: 4)
MVADEEAQLHAQAWDHALSYIKPTALSAAVELEIPDILENHGGPMTLSEL

SAASGCPREPLYRLMRFLIFHGIFTKSDDCYAQSPLSRLFTTENLGPYML

MQATPVTRCPTGLSGEALKTGTSLYLKSIRGEDSWSDPAYGYHMKAFTNA

MTAHARLTAAAIVRNYPAAFDGVQSVVDVGSRHGTAIGKLVEAFPWVRGI

AFDLPEIVADAPPRKGVDFVGGDMFESVPKADAVMLMWILHDWSDDKCIE

ILKKCKEAIPANIGKVMIVDAIINEDGEGDEFSGTRLSLDMIMLAVMAQG

KERTYKEWVHLLNEAGFSKHTIKNIKAMEFVIEAYP;

ObF8OMT-1 (AGQ21572.1 flavone 8-O-methyltransferase
[Ocimum basilicum])
                                       (SEQ ID NO: 5)
MPSSSGVDSTQELLDAQAHIWNHIFNHINSMTLKWAVQLGIPDIIHKHDK

PMTLSQLADAIPINRAKSDALHRIMRILVHSKFFDRVRTLPNEEEAYCLT

RASRLLLRDEPLSLTPFALAVLDEDLMGTFHCVPEWFGNECPSPLEFKHE

KSIREFAENNQRWSLLFNEGMANDARLVGSILAKESRKVFEGLETMVDVG

GGTGMVSKAIVDAFPGMKGIVLDLPYVVSGLKGSGNLRYVGGDMFHSVPP

ADAVFLKWILHNWSDDECIKILEKCKEAITTSKNMKGGKVIIVDMILGYE

KQQDEAVETQLFFDMMMMTTLTGKERTEQEWAKIFFAAGFKTYKIYPLLG

LRSLIEVFP;

ObF6H-1 (AGF30364.1 CYP450 monooxygenase CYP82D33
[Ocimum basilicum])
                                       (SEQ ID NO: 6)
MEFISFVYTLIAFSSLLYFYLIWSESAKPKTTTHKAPPEASGAWPVIGHL

RIMSGHPSAGIPHVNLGMLADKHGPIFSIRLGVHRVVVVSSPEVIKELFT

TNDVAVSSRPSVKAGKHLAYDNAMLGFASYGAYWRQLRKIVSLELLSNRR

LELQSHVSMSETGQFVKELYKLWEKKKSDGSGTEVGEGVVVDMKRWLGEL

NMNVVMRMVAGKRFGSGDNAEETKRCRRVMGDFFYLAGFFVPADALPYLG

WLDLGGHEKRMKKAAKELDEVVGEWLAEHREREFSGEGKAQDFMDVMISV

VKGADLQCEFDVDTIIKATCGTLIAGGTDTTAVVFVWALSLLLNHSHVLK

KAQQELDKHVGKDRRVKESDLNNLIYLQAIVKETLRLYPPGPLAGTRRFT

EDCVVGGYYIPKDTWLIVNLWKLQRDPRVWSDPLEFRPERFLAGDKTFDV

KGQDFELIPFGAGRRICPGLSFGLQMLHLVLASLLQAFDMSTVSDEAVDM

SESAGLTNMKATPLDVVVTPRLPPRLYNEIVEIY;

ObF8H-1 (AII16849.1 flavone 8-hydroxylase
[Ocimum basilicum])
                                       (SEQ ID NO: 7)
MPFPMEVLQASSLSFPLLRRHSRNNLINKFRNPTLPRIDIPRQNIDLKTF

AATTPTVACPPSDPEIIPEKKEDKFDWYENWYPVATVCDLDKRRPHGRKV

IGIDVVVWWDRKENAWKVFDDTCPHRLAPLSEGRIDQWGRLQCVYHGWCF

DGVGACKFIPQAPHDGPPVETSKKACVKGVYPSCVRNGIVWFWPNSDPKY

KDIYLTNKPHYIPELDDPSFTCTTITREVPGYGYEILAENLMDPSHVPYAH

YGILELEKVKESSKRDREGGHEMEISVGTIDVNGFSAKHVSADYYFVPPY

VYYGRITPNAATKTKDATLPVVPEEKTAMIVFYCIPVTPGYSRLIYAGAR

NFAVQIDRFVPRWITHMSHNLIFDSDLFLLHVEEQKLKDLDWHKSCYIPT

KADGQVVAFRRWLNKYGGTQVDWRNNFTPALPPTPSREQLFDRYWSHTAE

CSSCSVACKRLNALEIGLQAMSLVFVAMAAAVSAPATRYSMVAMAVLSFL

ASKWLSHFIHKTFYNHGYDHAFV;
```

-continued

ObFdx (AII16854.1 ferredoxin [Ocimum basilicum])
(SEQ ID NO: 8)
MATTQLPSNTAIKSALQNQIASPFVKLPVSLGSVKRATKAFGLTAKPNFR

ASAMATYKVKLIGPDGEESEFEAPDDCYILDSAEAAGVELPYSCRAGACS

TCAGKVASGSVDQSDGSFLDEKQMEEGYLLTCVSYPTADCVIHTHKESDL

Y;

ObFNR (AII16855.1 ferredoxin-NADP(+) reductase,
partial [Ocimum basilicum])
(SEQ ID NO: 9)
LAQVPVAVSVKNDVSLRSSVFKSNNVSFHETSRASRLSMDFRATSFKSRS

QPVVCMSVQQASKSKVAVSPLSLEDAKDPPLHLFKNKEPYEGTIVSVERL

VGPQAPGETCHIVIDHGGKVPYWEGQSYGIIPPGENPKKPGNPHNVRLYS

IASTRYGDSFDGKTASFCVRRAVYYDPETGKEDPSKKGVCSNFLCDSKPG

DKVQITGPSGKIMLLPEDDPKATHIMIATGTGVAPFRGYLRRMFMEDVPT

FKFNGLAWLFLGVANKDSLLYDDEFSKYLQDYPDNFRFDRALSREQKNRN

GGKMYVQDKIEEYSDEVFKLLDNGAHIYFCGLKGMMPGIQDTLKKVAEQR

GENWEEKLSQLKKNKQWHVEVY.

The amino acid sequences of the proteins disclosed herein may be altered and still be suitable for use. In other words, the sequences need not be identical to the sequences as disclosed herein by SEQ ID NO. For example, certain conservative amino acid substitutions may be made without having a deleterious effect on enzyme activity. A conservative substitution is one in which an amino acid is substituted for another amino acid that has similar properties, such that one skilled in the art of peptide chemistry would expect the secondary structure and hydropathic nature of the polypeptide to be substantially unchanged. In some exemplary aspects, the following groups of amino acids represent conservative exchanges/substitutions: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; and (5) Phe, Tyr, Trp, His. For example, conservative substitutions such as the following are tolerated: substitution of one positively charged amino acid for another positively charged amino acid; substitution of a negatively charged amino acid for another negatively charged amino acid; substitution of a hydrophobic amino acid for another hydrophobic amino acid; etc. All such substitutions or alterations are encompassed herein, as long as the resulting sequence still functions as described herein. Versions of the sequences presented herein with one or more deletions are also encompassed, e.g. versions from which about 1-5 (e.g. about 1, 2, 3, 4, or 5) consecutive amino acids have been deleted, are also encompassed, as long as the physiological function of the enzyme is not impaired. Such deletions may be truncations e.g. located at the amino or carboxyl terminus, or internal deletions within a sequence. In addition, in some aspects, altered or variant sequences may contain an insertion of e.g. from about 1-5 amino acids (e.g. 1, 2, 3, 4, or 5 amino acids), and still be tolerated, as long as the physiological function of the enzyme is not impaired. Insertions may be made e.g. at the amino terminus, the carboxyl terminus, within a sequence, or between epitope sequences. Amino acid sequences that are substituted, truncated or have an insertion are typically referred to herein as "based on" or "derived from" or "variants of" the original sequence.

Examples of changes/variations include but are not limited to: elimination or introduction of a protease cleavage site; changes which increase or decrease solubility (e.g. changes to hydrophobicity, etc.); changes which increase or decrease intra- or inter-molecular interactions; and so on, which are effected by adding or removing one or more amino acids that participate in such interactions. In some aspect, the changes avoid or decrease such interactions; in other aspects, the changes promote or increase such interactions. All such changes are intended to be encompassed by the present invention, so long as the resulting enzyme catalyzes the intended reaction.

In general, altered (variant) sequences exhibit at least about 50% to 99% identity or similarity to a corresponding sequence in the native enzyme, e.g. about 60 to 70, or 70 to 80, or 80 to 90, or 90 to 99% identity/similarity (e.g. about 90, 91, 92, 93, 94, 95, 96, 98, or 99% identical or similar to the wild type sequence. In some aspects, the altered sequence is about 95 to 100% identical/similar, e.g. about 95, 96, 97, 98 or 99% identical/similar. Percent sequence identity or similarity has an art recognized meaning and there are a number of methods to measure identity/similarity between two polypeptide or polynucleotide sequences. See, e.g., Lesk, Ed., Computational Molecular Biology, Oxford University Press, New York, (1988); Smith, Ed., Biocomputing: Informatics And Genome Projects, Academic Press, New York, (1993); Griffin & Griffin, Eds., Computer Analysis Of Sequence Data, Part I, Humana Press, New Jersey, (1994); von Heinje, Sequence Analysis In Molecular Biology, Academic Press, (1987); and Gribskov & Devereux, Eds., Sequence Analysis Primer, M Stockton Press, New York, (1991). Methods for aligning polynucleotides or polypeptides are codified in computer programs, including the GCG program package (Devereux et al., Nuc. Acids Res. 12:387 (1984)), BLASTP, BLASTN, FASTA (Atschul et al., J. Molec. Biol. 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (Adv. App. Math., 2:482-489 (1981)). For example, the computer program ALIGN which employs the FASTA algorithm can be used. Variant enzymes can generally be identified by modifying one of the enzyme sequences of the disclosure, and evaluating the properties of the modified proteins to determine if it is a biological equivalent. A variant is a biological equivalent if it retains e.g. 90-110% of the activity of the original protein e.g. retains the ability to catalyze the corresponding reaction.

Flavonoids that are Produced

The disclosed yeast strains and methods may be used to produce a wide variety of desirable flavonoids, examples of which include but are not limited to: acacetin, apigenin-7, 4'-dimethyl ether (AdM), dimethylated cirsimaritin (CIRM), cirsiliol (CIRL, 3'-OH-CIRM), 8-hydroxysalvigenin (8HS), gardenin B, genkwanin (GENK), ladanein (LAD), scutellarein-7-methyl ether (S7Me), pedalitin (PED), nuchensin (NUCH), trimethylated salvigenin (SALV), 8-substituted derivatives of SALV e.g. 8-hydroxysalvigenin, gardenin B, etc. Stereoisomers of the flavonoids are also encompassed. It is noted that these flavonoids may be recovered as end products for use outside a biosynthetic pathway, or used as substrates and further modified in a biosynthetic pathway, e.g. a pathway in which they are an intermediate.

In some aspects, the product that is produced is or is not cinnamic acid, p-coumaric acid and/or naringenin coumaryl: CoA. In other aspects, the product that is produced is or is not chrysin, apigenin, pinocembrin, naringenin, eriodictyol and/or luteolin.

It is noted that the appropriation of plant enzymes by yeast cells can result in the production of flavonoids that are not typically produced by the enzymes when present in plant cells. For example, the SALV yeast strain (designed to accumulate SALV as the major end product) was probed for biodiversification by feeding the cells with three additional compounds representing different flavonoid subclasses. The results showed that the constructed strain produced a number of rare compounds not reported to occur in the plant from which the genes were obtained (basil).

Genetic Engineering of Yeast

The recombinant yeast strains described herein are produced by genetic engineering techniques. Methods of genetically engineering (e.g. transforming) yeast to contain and express exogenous (heterologous, foreign, etc.) genes (i.e. a gene or genes which is/are not found in yeast in nature) are known in the art, and any such method may be used to practice the methods disclosed herein. The genes are typically housed in at least one expression vector, such as a plasmid, phagemid, a phage, cosmid, etc. For example, the circular 6.3-kb natural yeast plasmid may be used. This plasmid, which has a circumference of 2 has become known as the "2-micron" plasmid and is transmitted to the cellular products of meiosis and mitosis.

Other suitable vectors include derivatives of bacterial plasmids into which a yeast locus of interest has been inserted, together with a gene or genes of interest. When transformed into yeast cells, these plasmids insert into yeast chromosomes, generally by homologous recombination with the resident gene via either a single or a double crossover. As a result, either the entire plasmid is inserted or the targeted allele is replaced by the allele on the plasmid. The genes are therefore expressed over the lifetime of the yeast and are stably passed to progeny. However, methods which result in transient expression are also encompassed, as long as the heterologous genes are expressed for a useful period of time, e.g. for the intended time period of culturing the yeast.

Examples of suitable yeast transformation methods include but are not limited to: spheroplast methods, lithium methods, electroporation, biolistic methods, etc.

Yeast transformation methods are described, for example, in issued U.S. Pat. No. 7,338,791, as are methods of cultivating yeast. The complete contents of U.S. Pat. No. 7,338,791 are hereby incorporated by reference in entirety.

Cultivation of Recombinant Yeast

The medium used for culturing the yeast cells may be any general medium that is suitable for yeast cell growth, such as a minimal or complex medium containing proper supplements. The suitable medium may be commercially available or prepared by a known preparation method. The medium used for culturing may be a medium that satisfies the requirements of a particular yeast cell. The culture medium may include e.g. a carbon source, a nitrogen source, etc. Examples of carbon sources include but are not limited to monosaccharides, disaccharides, or polysaccharides. The carbon source may be glucose (e.g. about 2%), fructose, mannose, or galactose. The nitrogen source that may be utilized by the yeast cell may be an organic nitrogen compound or an inorganic nitrogen compound. The nitrogen source may be exemplified by amino acids, amides, amines, nitrates, or ammonium salts.

In some aspects, the culture medium is a "rich medium" such as rich YP medium (10 g·L$^{-1}$ each of yeast extract and peptone). Rich medium is used because the cells grow better (e.g. than in selection media), and the yields are higher. In some aspects of the strains described herein, the expression of heterologous genes is induced by the addition of galactose to the media, and is repressed in the presence of glucose. Thus, in some aspects, glucose is not included in (or is excluded from) the medium, and in some aspects, galactose is added to the rich medium.

In some aspects, depending on the yeast strain that is employed, selection medium may be used e.g. media minus one or more components such as histidine, tryptophan, leucine, uracil, etc. Further, during the culturing of a yeast, the conditions may be changed. For example, a yeast may be grown to high density and/or high enzyme production using one type of media and then switched to a production phase, e.g. by the addition of one or more substrates and/or by furnishing nutrients that have become depleted, by adding an expression inducer (such as galactose), etc.

The yeast strains are typically cultured with at least one substrate, examples of which include but are not limited to: apigenin, naringenin, luteolin, kaempferol, etc. Also, any compound described herein as produced by the recombinant yeasts may also be used as a substrate, provided the compound is an intermediate that is further modified by an enzyme of the pathway.

The culturing conditions are controlled in order to obtain flavonoids and/or flavonoid intermediates from the genetically engineered yeast cell. For proliferation, the cell is generally cultured under aerobic conditions. The yeast is generally cultured at a temperature of from about 25 to about 35° C., e.g. about 29° C., for a period of time ranging from about 8 to about 24 hours or longer, e.g. for about 1-7 days, such as for about 1, 2, 4, 5, 6, or 7 days. Aeration of the cultures may be achieved e.g. by agitation, shaking, etc.

Recovery of Flavonoids

Recovery of flavonoids from the culture may be performed by isolation using a general method known in the art. Such isolation methods may include centrifugation, filtration, chromatography, crystallization, etc. For example, the culture may be centrifuged and or filtered to remove biomass, and the resulting supernatant may be subjected to chromatography for isolation.

In some aspects, a high proportion of product is retained in the cells so if centrifugation is used to remove the cells and they are then discarded, a substantial amount of the product is lost. Thus, in some aspects, the cell suspensions (cells and spent medium) are extracted with a solvent such as ethyl acetate, and the solvent is then evaporated (e.g. in vacuo or using $N_2$. Subsequently, methods like TLC or LC-UV can be used to isolate the pure compounds.

Uses and Products

The flavonoids that are produced as described herein may be used in any of a variety of products. For example, they may be used as nutraceuticals, in food products, as dietary supplements, in products for external application, e.g. in cosmetics, lotions, hair care products, etc. One or more than one flavonoid may be included in a product. All products and uses of the flavonoids produced as described herein are encompassed by this disclosure.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise.

In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

When a list is prefaced by, for example, "include but are not limited to" what is intended is that one or more of the elements listed may or may not (is or is not) included.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1. Production of Methoxylated Flavonoids in Yeast Using Ring a Hydroxylases and Flavonoid O-Methyltransferases from Sweet Basil In the past few years, the biosynthesis of methoxylated flavonoids in trichomes of sweet basil (*Ocimum basilicum*) have been elucidated. Flavones substituted at position 6 or both 6 and 8, and carrying up to four methyl moieties at positions 6, 7, 8, and 4' occur in this tissue. A set of regioselective FOMTs with distinctive properties and regiospecific flavonoid 6- and 8-hydroxylases were identified. (Berim and Gang 2016). To obtain commercially unavailable substrates for the present work, appropriate hydroxylase(s) and FOMTs were combined and five *Saccharomyces cerevisiae* strains that are designed to produce flavones found in basil when fed API as substrate were constructed. The flavones produced (and the corresponding strain designation) are the dimethylated cirsimaritin (CIRM) and ladanein (LAD), trimethylated salvigenin (SALV), and 8-substituted derivatives of SALV, 8-hydroxysalvigenin (8HS) and gardenin B (GB) (FIG. 1).

Initially, different growth conditions and periods were compared using the SALV strain (designed to accumulate SALV as the major end product; the same nomenclature is used to refer to the other strains included in this disclosure). The utility of these yeast strains was probed for biodiversification by feeding the cells with three additional compounds representing different flavonoid subclasses. These experiments revealed that the constructed strains can be used to produce a number of rare compounds not reported to occur in basil, and that the substrate specificity both of the FOMTs and the flavonoid hydroxylases restricts the product yields.

Materials and Methods

Chemicals:

All general chemicals used were of analytical grade and obtained from common vendors (Fisher, VWR, Sigma). Flavonoids fed as precursors were from Indofine except for NAR which was from Sigma Aldrich. Yeast nitrogen base without amino acids and appropriate amino acid mixes for the preparation of drop-out media were purchased from United States Biological.

Construction of Expression Plasmids pESC vector series (Agilent) were used for the expression of all plant genes, and *S. cerevisiae* strain INVSc-1 (Invitrogen™) was used as expression host. A summary of all cloning details including all primer sequences, corresponding vectors and strains where they are used is shown in Table 1. As described earlier, all components of the basil flavonoid 8-hydroxylase system were expressed as fusions with yeast Yah1p mitochondrial transit peptide (Berim et al. (2014) Plant J 80:385-395). All constructs were validated by direct sequencing.

TABLE 1

Sequences of primers used for cloning, and list of vectors harboring the open reading frames, and corresponding strains carrying the vectors. Restriction sites are shown in italics, start and stop codons are underlined.

| # | primer name | protein, | sequence (5' → 3') |
|---|---|---|---|
| 1 | ObFOMT1-F | ObFOMT1 | ATA*CTAGT*A̲T̲G̲GGGCGGGACGAAGAGGC (SEQ ID NO: 10) |
| 2 | ObFOMT1-R | | ATC*ATCGAT*T̲C̲A̲GGGATAAGCCTCAATGAGTG (SEQ ID NO: 11) |

TABLE 1-continued

Sequences of primers used for cloning, and list of vectors harboring the open reading frames, and corresponding strains carrying the vectors. Restriction sites are shown in italics, start and stop codons are underlined.

| | | | |
|---|---|---|---|
| 3 | ObF6H-1-F | ObF6H-1 | *ACTAGT*<u>ATG</u>GGAATTCATCTCGTTTGTCTACACCCTC (SEQ ID NO: 12) |
| 4 | ObF6H-1-R | | AT*CATCGAT*<u>TCA</u>ATAAATCTCAAcGATCTCATTATAGAGT (SEQ ID NO: 13) |
| 5 | ObFOMT4-F | ObFOMT4 | ATA*CTAGT*<u>ATG</u>GCGGTAGACAAAGAAGTTGA (SEQ ID NO: 14) |
| 6 | ObFOMT4-R | | AT*CATCGAT*<u>TCA</u>AGGATAAGCCTCAATTACAA (SEQ ID NO: 15) |
| 7 | ObFOMT5-F | ObFOMT5 | *ACTAGT*<u>ATG</u>GTGGCAGACGAAGAAGCCCAACTT (SEQ ID NO: 16) |
| 8 | ObFOMT5-R | | *ATCGAT*<u>TCA</u>AGGATAGGCCTCAATCACAAACTC (SEQ ID NO: 17) |
| 9 | ObFOMT3-F | ObFOMT3 | *ACTAGT*<u>ATG</u>GCGGTAGACAAAGAAGTTCAA (SEQ ID NO: 18) |
| 10 | ObFOMT3-R | | *ATCGAT*<u>TCA</u>AGGATAGGCCTCAATCACGGACTC (SEQ ID NO: 19) |
| 11 | ObF8H-yah1-F | ObF8H-1 | *GGATCC*<u>ATG</u>TTGTTCTATAAGCCTGTGATGAGGATGGCGGTGAGACCGCTAAAAAGCATAAGATTCCAGGCCGCGACTACTCCGACTGTCGCGTG (SEQ ID NO: 20) |
| 12 | ObF8H-1 R | | *GGATCC*<u>TCA</u>GACAAAGGCATGATCATAACCATG (SEQ ID NO: 21) |
| 13 | Fdx-yah1-F | ObFdx | *GCGGCCGC*<u>ATG</u>TTGTTCTATAAGCCTGTGATGAGGATGGCGGTGAGACCGCTAAAAAGCATAAGATTCCAGTCCTCAGCAATGGCAACATACAAGGT (SEQ ID NO: 22) |
| 14 | Fdx-y-R | | *ACTAGT*<u>CTA</u>ATACAAATCACTCTCCTTGTGAGTG (SEQ ID NO: 23) |
| 15 | FNR-yah1-F | ObFNR | *GGATCC*<u>ATG</u>TTGTTCTATAAGCCTGTGATGAGGATGGCGGTGAGACCGCTAAAAAGCATAAGATTCCAGTCCTCCGTGCAACAAGCCAGCAAATC (SEQ ID NO: 24) |
| 16 | FNR-y-R | | *GGATCC*<u>TCA</u>GTAAACCCTCAACATGCCATTGTTTT (SEQ ID NO: 25) |
| 17 | ObF8OMT-1F | ObFOMT8-1 | *CTCGAG*<u>ATG</u>CCATCATCCAGTGGAGTAGATTC (SEQ ID NO: 26) |
| 18 | ObF8OMT-1R | | *GGTACC*<u>CTA</u>GGGGAAAACTTCAATTAAAGA (SEQ ID NO: 27) |

| # | vector | resulting vector | strain(s) | restriction sites |
|---|---|---|---|---|
| 1 2 | pESC-TRP | pESC-TRP-ObFOMT1 | All but GB | SpeI/claI |
| 3 4 | pESC-URA | pESC-URA-ObF6H-1 | all | SpeI/ClaI |
| 5 6 | pESC-HIS | pESC-HIS-ObFOMT4 | CIRM | SpeI/ClaI |
| 7 8 | pESC-HIS | pESC-HIS-ObFOMT5 | LAD | SpeI/ClaI |
| 9 10 | pESC-HIS | pESC-HIS-ObFOMT3 | SALV, 8HS, GB | SpeI/ClaI |
| 11 12 | pESC-Leu2d | pESC-Leu2d-ObF8H-1 | 8HS, GB | 2xBamHI |
| 13 14 | pESC-Leu2d-ObF8H-1 | pESC-Leu2d-ObF8H-1-ObFdx | 8HS, GB | NotI/SpeI |
| 15 | pESC-HIS-ObFOMT3 | pESC-HIS-ObFOMT3-ObFNR | 8HS, GB | 2xBamHI |

TABLE 1-continued

Sequences of primers used for cloning, and list of vectors harboring the open reading frames, and corresponding strains carrying the vectors. Restriction sites are shown in italics, start and stop codons are underlined.

| 16 | | | | |
|---|---|---|---|---|
| 17 | pESC-TRP-ObFOMT1 | pESC-TRP-ObFOMT1-ObFOMT8-1 | GB | XhoI/KpnI |
| 18 | | | | |

Yeast Growth and Cultivation Conditions

Seed cultures were grown for 16-22 h at 29° C. and 210 rpm (New Brunswick C25KC shaker) in 30 mL appropriate selection medium (SD minus HIS, TRP, URA for CIRM, LAD and SALV strains, and SD minus HIS, TRP, URA, LEU for strains 8HS and GB) with 2% glucose. The main cultures were 10 mL-aliquots of either appropriate selection or rich YP medium (10 g·L$^{-1}$ each yeast extract and peptone) either in 125 mL Erlenmeyer flasks or in 50 mL vertically positioned conical tubes, with 2% galactose in all cases, and were inoculated with 1 mL of seed culture ($OD_{600}$ at 1:20 dilution=0.5). All substrates were supplied at the time of main culture inoculation as 100 µL aliquots of 10 mM solutions in DMSO per culture vessel, with a final concentration of 100 µM. Main cultures were grown at 29° C. and 210 rpm. After removing the aliquots for analysis on day 2 and 4 of growth, 500 µL of 20% galactose solution were added to appropriate cultures. For the evaluation of alternative substrates, yeast cells were grown in rich medium and flasks, with a single harvest after 2 days of incubation with the fed precursor.

Cell densities were determined at 600 nm in 1:20 or 1:100 dilutions using a Lambda 35 spectrophotometer (Perkin Elmer). Calculation of cell numbers was based on colony counts after plating serial dilutions of a culture with known cell density.

Extraction of Fermentation Products

Aliquots of 500 µL culture broth with cells were removed from the culture vessels. When necessary, cells were separated from the culture medium by centrifugation at 21000 g for 1 min. The supernatants were then transferred to another plastic tube while the cell pellet was suspended in 500 µL water. All samples were acidified with 25 µL 6N HCl and extracted twice with 550 µL ethyl acetate. Combined organic fractions were dried in a centrifugal vacuum concentrator. The residues were dissolved in 200 µL 50% aqueous methanol with 0.1% formic acid, containing 25 µM quercetagetin (Extrasynthese) or 7,8,3',4'-tetrahydroxyflavone (Indofine) as the internal standard.

Flavonoid Analysis by LC-MS

A Synapt G2-S quadrupole-ion mobility spectrometry-time of flight mass spectrometer system (WATERS®) equipped with an ACQUITY UPLC® system with a photodiode array detector was used for LC-MS analysis of extracts. Extracted metabolites were separated on an ACQUITY UPLC® BEH C18 column (50 mm length, 2.1 mm diameter, particle size 1.7 µm) using acetonitrile with 0.1% formic acid as solvent B and water with 0.1% formic acid as solvent A at a flow rate of 400 µL min$^{-1}$ and the following linear gradient extending over 14 min: 0 min, 3% B; 1.86 min, 5% B, 6.86 min: 35% B; 9.69 min, 100% B; 10.52 min, 100% B; 11.02 min, 3% B; 14 min, 3% B. Mass spectra were collected in positive mode over a range of m/z 50-1000 with a scan time of 0.2 s. The capillary was set at 3 kV, the sampling cone at 40V, the source at 120° C., and the desolvation temperature at 250° C. Cone gas and desolvation gas flows were 0 and 850 L·h$^{-1}$, respectively. The collision energy for MS/MS fragmentation was 30 V. Calibration accuracy cutoff was 1 ppm. Leucine enkephalin was used for post-acquisition mass (lock mass) correction. UV data were collected over a range of 210-500 nm. Quantification of products was carried out using the UV data and calibration curves for the corresponding fed substrate under the previously validated assumption that the extinction coefficient for band I does not change significantly with methylations/6-hydroxylation (Grayer et al. (1996) Phytochemistry 43:1041-1047). The wavelengths used correspond to band I UV maximum of individual substrates (335, 345, 290, and 366 nm for API, LUT, NAR and kaempferol (KAEM), respectively). All concentrations were recalculated to milligram per liter of culture from the 10 mL batches. Quantitative analysis was conducted using the TargetLynx module of MassLynx™ v.4.1. Statistical analysis was performed using STATISTICA™ 13 (TIBCO®) and SPSS® Statistics 23 (IBM®).

Results

Strains Producing CIRM, LAD, SALV, 8HS and GB from API.

Combinations of previously characterized regioselective FOMTs with flavonoid ring A hydroxylases were used for strain construction. All strains harbored basil ObFOMT1, a flavonoid 7-O-methyltransferase (F7OMT) that very efficiently converts API into genkwanin (GENK, FIG. 1). All strains also expressed the basil flavonoid 6-hydroxylase (F6H) encoded by CYP82D33 (ObF6H-1). It converts its preferred substrate GENK into scutellarein-7-methyl ether (S7Me, FIG. 1). The other components varied between strains.

Figure 3B:
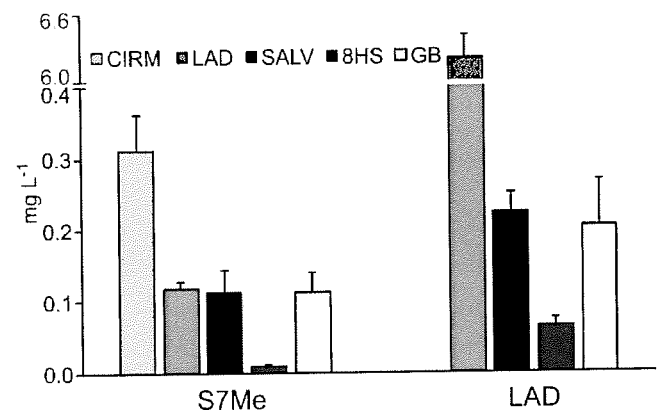

The strain producing CIRM additionally harbored ObFOMT4, which catalyzes the 6-O-methylation of S7Me. After two days of growth under preferred conditions described below the titer of CIRM was 12.1±1.7 mg-L$^{-1}$ (Table 2). ObFOMT4 only exhibits very low flavonoid 4'-O-methyltransferase (F4'OMT) activity when incubated with appropriate substrates such as GENK or CIRM for an extended amount of time. Therefore, the formation of byproducts apigenin-7, 4'-dimethyl ether (AdM) and SALV is minimal in this strain (FIG. 2, FIG. 3). One readily detectable byproduct is GENK (FIG. 3), the product of the initial API 7-O-methylation that has not been completely 6-hydroxylated.

TABLE 2

Overview of flavonoid accumulation by the five yeast strains supplied with different substrates.

| substrate fed | strain | | | | |
|---|---|---|---|---|---|
| | CIRM | LAD | SALV | 8HS | GB |
| apigenin | 12.1 ± 1.7 | 6.2 ± 0.2 | 5.0 ± 0.9 | 0.8 ± 0.0 | 0.4 ± 0.1 |
| naringenin | 1.9 ± 0.3 | 1.6 ± 0.5 | 0.6 ± 0.1 | n.q. | n.q. |
| luteolin | 1.7 ± 0.2 | 0.7 ± 0.0 | 0.4 ± 0.2 | n.q. | n.q. |
| kaempferol | n.q. | n.q. | n.q. | n.d. | n.d. |

Concentrations (mg · L$^{-1}$) of main products (eponymous with the strain names for apigenin, and corresponding derivatives with other fed precursors) extracted from whole cell suspensions after two days of main culture growth in rich medium and flasks. Results are means ± standard deviation (n = 3).
N.q.: not quantified;
n.d.: not detected.

Instead of ObFOMT4, the strain producing LAD expressed ObFOMT5, an enzyme whose preferred substrate is S7Me and which is strongly selective for the 4'-OH moiety as acceptor. After two days of fermentation, the concentration of LAD was 6.2±0.2 mg·L$^{-1}$ (Table 2). ObFOMT5 is active with GENK, and also shows some F6OMT activity with LAD. The accumulation of the byproduct AdM (and a small signal for SALV) is therefore readily detectable at UV$_{335}$ (FIG. 2, FIG. 3).

The strain producing trimethylated SALV expressed ObFOMT3 as the only FOMT other than ObFOMT1. This enzyme shares 92% identity with ObFOMT5 and acts primarily as the F4'OMT of S7Me in planta. However, in contrast to ObFOMT5, ObFOMT3 has significant 6-O-methylating activity with LAD (17.06% relative to turnover with S7Me). By taking advantage of this bifunctional F6/4'OMT, we aimed to circumvent the need of using a separate F6OMT such as ObFOMT4. The concentration of SALV reached 5.0±0.9 mg·L$^{-1}$ after two days of growth (Table 2). As is the case with ObFOMT5, ObFOMT3 displays F4'OMT activity with GENK, leading to accumulation of AdM as byproduct (FIG. 2, FIG. 3).

The strains producing 8HS and GB were derived from the SALV strain. They both additionally harbored three enzymes necessary for the 8-hydroxylation of SALV. Basil flavone 8-hydroxylase (F8H) is a Rieske-type oxygenase that requires reduced ferredoxin (Fdx) as an electron donor. In turn, Fdx is reduced by Fdx-NADP$^+$ reductase (FNR). Constructs encoding all three plant enzymes had to be introduced into yeast cells as the activity of ObF8H-1 in this host is extremely low in the absence of its native redox partners. The 8HS strain accumulated 8HS at a titer of 0.81±0.04 mg·L$^{-1}$. In comparison to the 8HS strain, the strain producing GB additionally harbored the basil flavonoid 8-O-methyltransferase (F8OMT) designated ObF8OMT-1. The yield of GB was 0.44±0.12 mg·L$^{-1}$ (Table 2). Both strains accumulated AdM and SALV as byproducts (FIG. 2, FIG. 3).

Characterization of Flavone Accumulation in the SALV Strain

Figure 4:
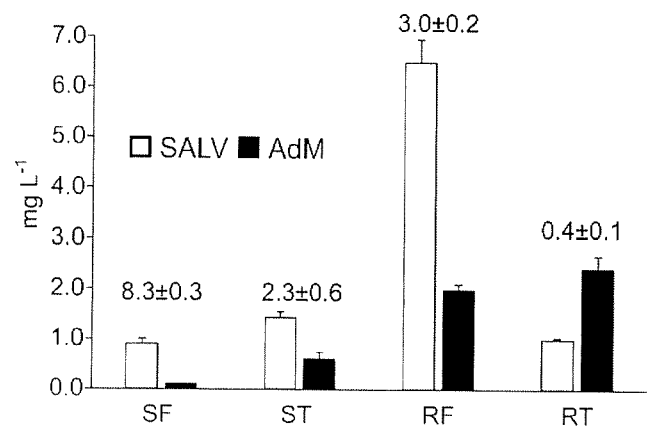
FIG. 4. Flavone production under different fermentation conditions. SALV-producing yeast cells were supplemented with API and grown for two days in selection medium and shake flasks (SF), selection medium and conical tubes (ST), rich medium and shake flasks (RF), or rich medium and conical tubes (RT). Numbers above bars show molar SALV/AdM ratio. Error bars represent standard deviation (n=3).
Figures 5A, 5B, 5C, 5D:
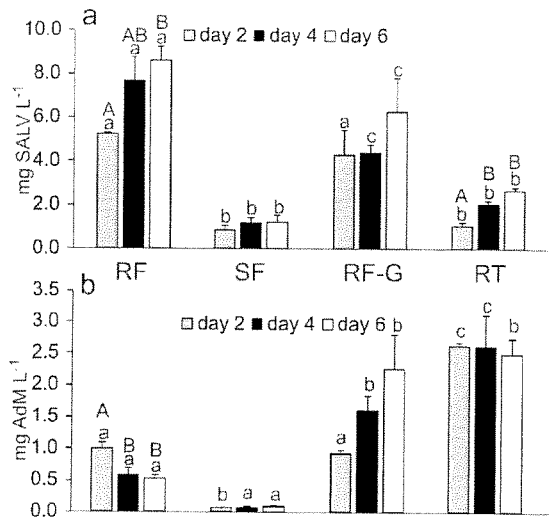
FIG. 5A-D. Comparison of growth conditions using the SALV strain. A, accumulation of SALV; B, accumulation of AdM; C, molar SALV/AdM ratios; D, cell numbers. Error bars represent standard deviation (n=3). Different lower case letters indicate the means differed significantly across treatments for the same time point. Different upper case letters indicate the means differed significantly across time for the same treatment (two-way mixed ANOVA, p<0.05). No upper case label indicates no significant differences were detected across time for a given treatment.
Figure 6A:
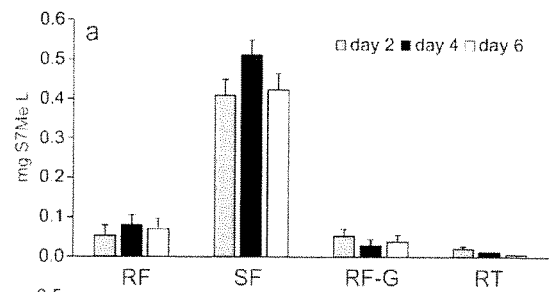
FIG. 6A-E. Comparison of growth conditions using the SALV strain. The SALV strain was grown in rich medium and flask (RF), selection medium and flask (SF), or rich medium and conical tube (RT) for six days, and supplemented with galactose on day 2 and 4 after inoculation except for treatment RF-G (grown in rich medium and shake flask). A, accumulation of S7Me; B, accumulation of LAD; C, accumulation of GENK; D, accumulation of SALV, normalized to cell numbers. E. Accumulation of AdM, normalized to cell numbers. Error bars represent standard deviation (n=3).
Figure 6B:
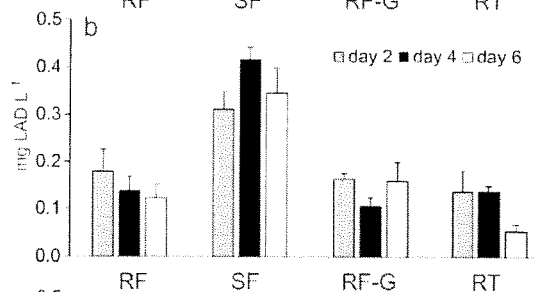
Figure 6C:
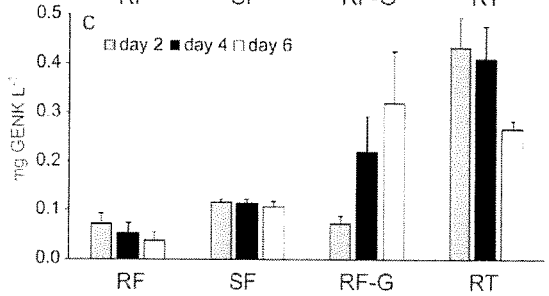

Prior to testing alternative substrates, we evaluated the effect of several basic growth parameters on product yields. These tests were conducted using the SALV strain. In an initial test, we compared four possible combinations of rich versus selection media and conical tubes (50 mL) versus unbaffled Erlenmeyer flasks (125 mL, with 10 mL medium in all conditions) in a bioconversion that lasted 48 hours. Cells growing in rich medium and shake flasks (treatment designated RF) accumulated the highest amounts of the desired product SALV and moderate amounts of the major byproduct AdM (FIG. 4) as compared to the other three treatments designated SF (selection medium/flask), RT (rich medium/tube) and ST (selection medium/tube). The product specificity was estimated by the molar ratio between the desired 6-hydroxylated product SALV and the byproduct AdM, and it was highest in SF cultures (FIG. 4). For the subsequent tests, the cultivation time was extended up to six days, and RF growth conditions were compared to SF and RT while ST treatments were not continued based on data shown in FIG. 4. To maintain the activity of the GAL promoters driving the expression of all heterologous genes, all cells except for the cultures designated RF-G (grown in rich medium and flasks) were fed with galactose on days 2 and 4 of incubation. After two days of growth, RF and RF-G cultures, which were treated identically to this time point, accumulated the highest amounts of SALV after two days of growth (FIG. 5A). SALV abundance increased by about 30% to day 4 in RF cultures, and did not increase significantly after an additional 48 hours of incubation. SALV yield was significantly lower in SF and RT cultures. The accumulation of SALV increased significantly throughout the monitored time course in RT cultures grown in conical tubes (FIG. 5A). The main byproduct, AdM, accumulated at highest levels in RT cultures (FIG. 5B). In RF cultures, its abundance was highest on day 2, and decreased with longer incubation. The apparent consumption of AdM confirms the ability of ObF6H-1 to hydroxylate this flavone. Analysis of biosynthesis intermediates revealed that LAD and S7Me were most abundant in SF cultures (FIGS. 6A and B) while GENK was most abundant in RT cultures (FIG. 6C).

The SALV/AdM ratio was highest in SF cultures on day 2. However, it increased significantly with extended growth time in RF cultures (FIG. 5C). The lowest SALV/AdM ratios were measured in RT cultures. The periodic addition of the expression inducer galactose seems to support SALV production and improve the SALV/AdM ratio, as suggested by a comparison between RF and RF-G cultures (FIG. 5A-C).

Figure 6D:
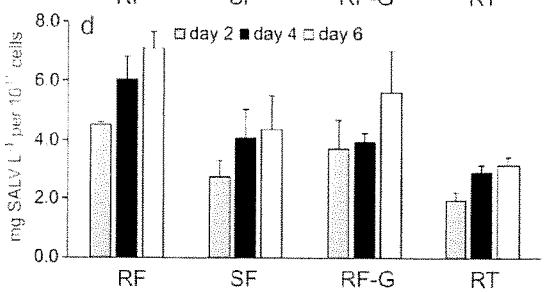
Figure 6E:
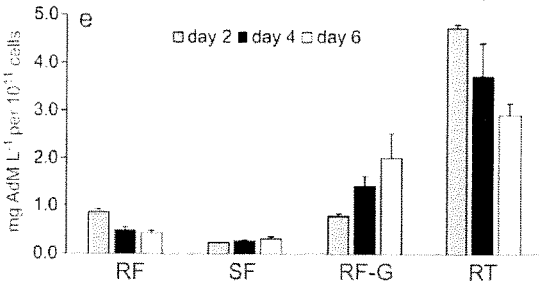

The cell growth was not equal under the different treatments (FIG. 5D). It was significantly slower in RT cultures as compared to RF cultures, and the cell numbers increased steadily throughout the incubation. It is possible that the cell growth in tightly capped tubes is restricted by oxygen supply, and the amount of nutrients suffices to sustain the cell growth at a lower rate but over a longer period of time. Notably, overall "per cell" yields of SALV together with AdM were similar between RF and RT cultures (FIGS. 6D and E). The cell growth was also slow in SF cultures, and no increase in cell numbers was observed over the monitored time period. The selection medium might thus be depleted after two days of growth.

Localization of Flavones During Bioconversion of API

Figure 7:
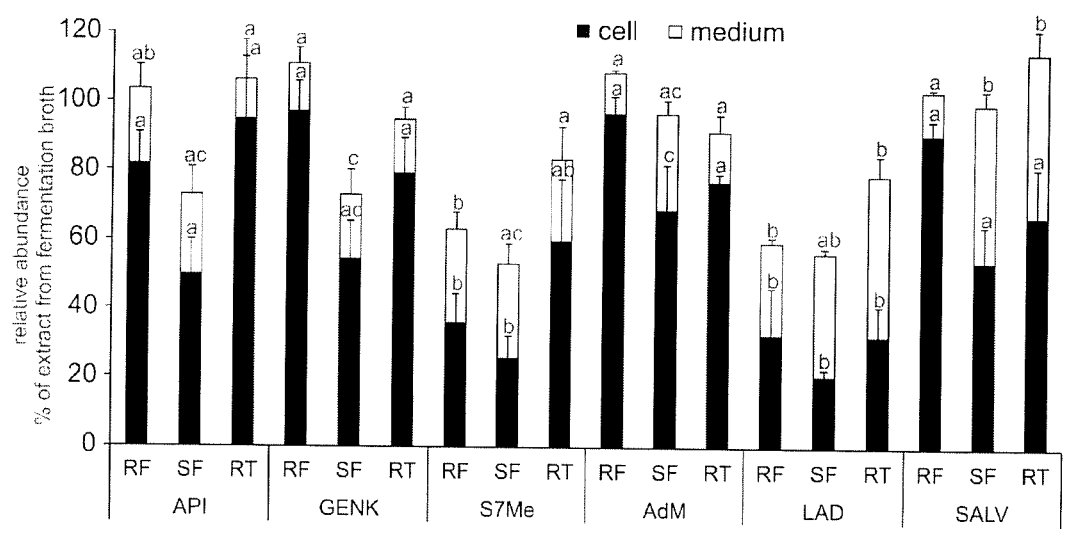
FIG. 7. Distribution of flavones between cells and medium in the SALV strain. The abundances of flavones were calculated as percent of abundance in extracts from fermentation broth containing both cells and medium after two days of incubation with API. Error bars represent standard deviation (11=3). Designations of culture conditions are RF=rich, flask; SF=selection, flask; and RT=rich, tube. Different lower case letters indicate the means differed significantly (comparison within the same fraction and treatment, one-way ANOVA, p<0.05).

To analyze the localization of the flavones during biofermentation, yeast cells were separated from the spent medium by centrifugation, and the two fractions extracted individually. SALV strain cells grown under RF, SF, and RT conditions were compared in this study. Approximately 90% (of the total amount extracted from whole cell suspension) of the main products SALV and AdM were found in yeast cells in RF cultures on day 2 after inoculation (FIG. 7). The fed substrate API also accumulated in yeast cells. Remarkably, the proportion of intracellularly accumulated AdM and SALV was significantly lower in cells of SF cultures. Analysis of pathway intermediates revealed that GENK was also strongly enriched in cells. By contrast, the relative abundances of LAD and S7Me in the medium were significantly higher than those of SALV, GENK and AdM in RF cultures. LAD content in the medium amounted to 30-40% of its abundance in whole cell suspension, S7Me content ranged at 30-50%. Notably, the content of LAD and S7Me in cells was conspicuously low, ranging 22-60% of total (and as a result, the relative abundances do not add up to 100% of the amount found in fermentation broth with cells, FIG. 7). Currently, we do not have an explanation for this observation, which has been made in a number of independent experiments. Overall, the high relative abundance of LAD and S7Me in spent medium suggests that partitioning and translocation of flavones involves certain selectivity, as both of these compounds accumulate at only low levels.

In a separate test, we analyzed the distribution of the main products in the SALV, CIRM, and LAD strains grown in parallel under RF conditions. The distribution of the fed substrate API was comparable across strains (overall 10-19% in the medium and 74-85% in cells). By contrast, CIRM partitioned nearly equally (40.5% medium/55.1% cells). As the main product of the LAD strain, LAD was more abundant in spent medium (60.2% medium/29.0%

Figure 10:
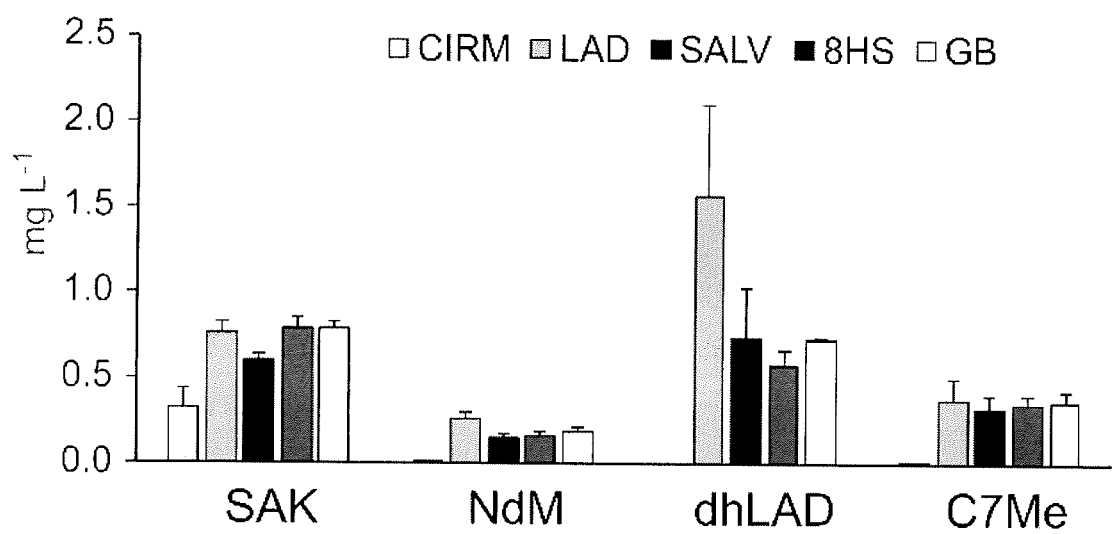
FIG. 10. Flavanone accumulation in yeast strains fed with naringenin as substrate. Abundances of SAK, NdM, dhLAD, and C7Me are reported after two days of fermentation. Legend indicates yeast strains. All abbreviations as in text.

The first biosynthetic intermediate, 7-methylnaringenin (sakuranetin, SAK), was readily detectable in all five strains. Its level was lower in the CIRM strain and about equal in the other four strains (FIG. 10). Remarkably, the flavanone analog of S7Me, carthamidin-7-methyl ether (C7Me), accumulated in high relative abundance (0.32-0.38 mg·L$^{-1}$) in all but the CIRM strain, where only traces of this intermediate were present (ca. 0.02 mg·L$^{-1}$). Naringenin-7,4'-dimethyl ether (NdM) also accumulated in all strains (with the CIRM strain only containing trace amounts, FIG. 10).

We analyzed the distribution of NAR and its fermentation products in the SALV strain and found that over 80% of NAR was present in the culture media (Table 3). By contrast, NdM and SAK were enriched in cells. Like their flavone analogs, C7Me and dhLAD were predominantly located in spent medium. Surprisingly, over 50% of dhSALV was also present in spent medium.

TABLE 3

Flavonoid distribution in the SALV strain. Distribution of alternative substrates and their bioconversion products in the SALV strain between yeast cells and spent medium.

| fed | substrate | | 7-O—Me | | 7,4'-O—Me | | 6-OH-7-O—Me | | 6-OH-7,4'-O—Me | | 6-OH-6,7,4'-O—Me | |
|---|---|---|---|---|---|---|---|---|---|---|---|---|
| substrate | M | C | M | C | M | C | M | C | M | C | M | C |
| NAR | 84 ± 2 | 16 ± 1 | 46 ± 8 | 75 ± 8 | 20 ± 6 | 94 ± 8 | 103 ± 8 | 1 ± 0 | 71 ± 5 | 3 ± 1 | 75 ± 13 | 57 ± 10 |
| LUT | 55 ± 2 | 54 ± 13 | 47 ± 9 | 61 ± 16 | 32 ± 4 | 88 ± 16 | 87 ± 6 | 11 ± 2 | 72 ± 6 | 17 ± 5 | 69 ± 6 | 49 ± 10 |
| KAEM | 21 ± 2 | 54 ± 4 | 20 ± 4 | 71 ± 8 | 19 ± 7 | 126 ± 9 | n.d. | n.d. | n.d. | n.d. | n.d. | n.d. |

Column headers indicate structural changes of the fed substrate occurring to yield the relevant derivative.
M: medium, C: cells.
All values are in % of the signal observed in extract from whole cell suspension, showing mean ± standard deviation (n = 3).
N.d. = not determined due to low product abundance.

cells), consistently with its location when monitored as a low-abundance intermediate of SALV biosynthesis in the SALV strain (FIG. 7). As expected based on the above results, SALV was enriched in cells (16.6% medium/77.4% cells).

Biofermentation Using Flavanone NAR as Fed Substrate

NAR differs from API by having a saturated C2-C3 bond (FIG. 1). As a result, the molecule has a chiral carbon (C2). Natural flavanones typically have the S configuration at this position. The substrate that we fed to yeast cells was an unspecified mixture of the two enantiomers.

Figure 8A:
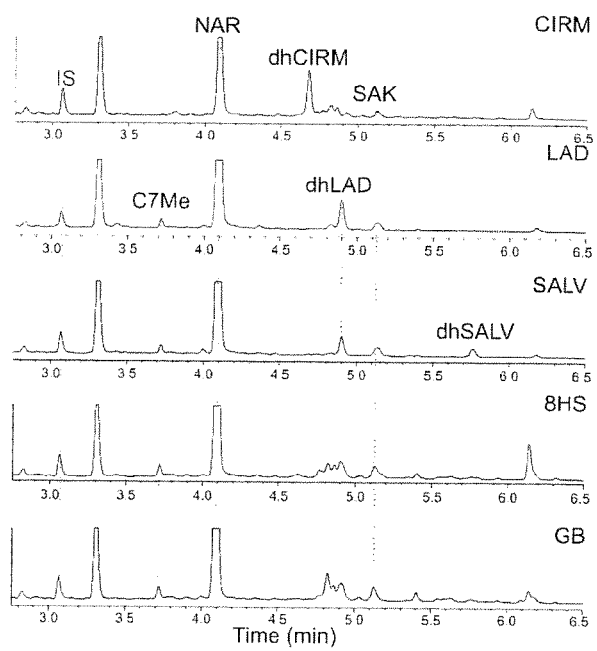
FIGS. 8A and B. Biofermentation of naringenin by the constructed yeast strains. A, $UV_{290}$ chromatograms of extracts from whole cell suspensions; B, selected ion chromatograms of the same extracts from 8HS and GB strains. Maximum peak height indicated in the upper right corner. Ion monitored is indicated in the upper left corner. All compound abbreviations as in text. Strains are indicated in the upper right corner. Vertical dotted lines connect the same metabolites across strains. IS=internal standard quercetagetin. NdM elutes at 6.13 min but the signal is compromised by co-eluting compounds in several traces and hence left unlabeled.

In the yeast fermentation system, all of the target dihydrogenated (abbreviated as dh) products, i.e. dhCIRM, dhLAD, dhSALV, dh8HS, and dhGB, were formed by their respective strains, but in differing amounts (FIG. 8, FIG. 9, FIG. 10, Table 2). The accumulation of dhCIRM reached a final level of 1.85±0.34 mg·L$^{-1}$. The titer of dhLAD reached 1.56±0.54 mg·L$^{-1}$ in the LAD strain. In the SALV, 8HS and GB strains, residual dhLAD accumulated at levels ranging from 0.57 to 0.74 mg·L$^{-1}$ (FIG. 10). The dihydro-derivative of SALV accumulated at 0.60±0.07 mg·L$^{1}$ in the SALV strain. Notably, its abundance in the 8HS and GB strains was only about 20% of the concentration in SALV strain, even though its downstream conversion to 8-hydroxylated products was quantitatively insignificant.

Figure 8B:
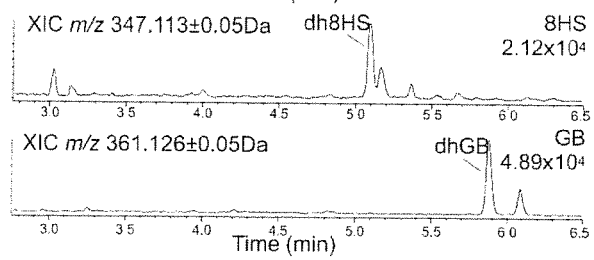
Figure 9A:
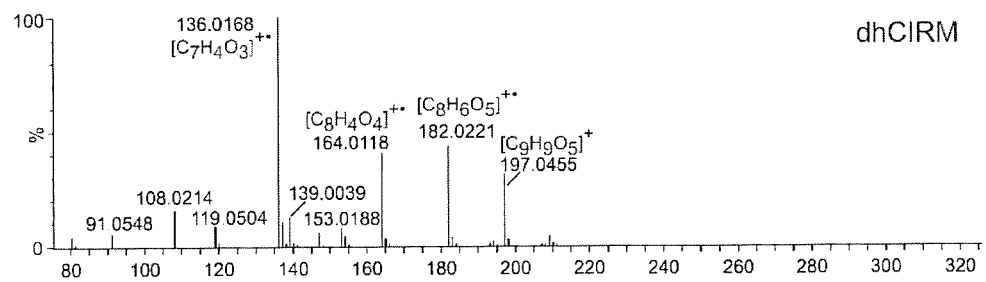
FIG. 9A-G. Identification of biofermentation products with NAR as fed substrate using MS. A-C, MS spectra of dhCIRM, dhLAD, and dhSALV collected at 30V collision energy. Compound is indicated in the upper right corner. D-G, predicted and observed isotope models and accurate masses of dh8HS and dhGB. Compound, formula of the [M+H]+ ion and mass error are shown in the upper right corner.
Figure 9B:
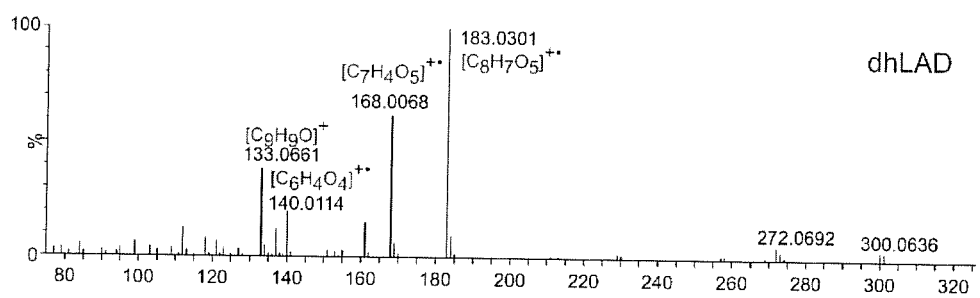
Figure 9C:
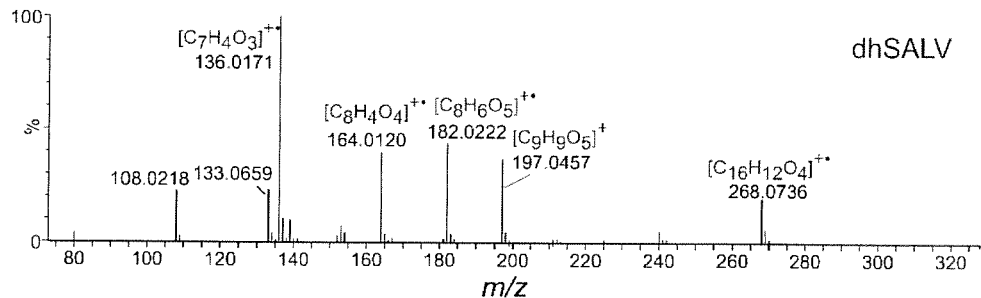
Figure 9D:
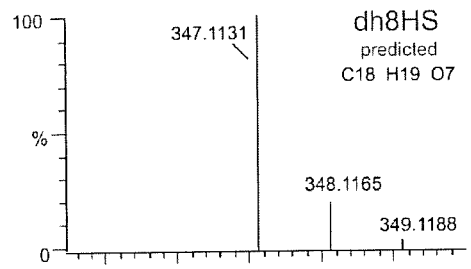
Figure 9F:
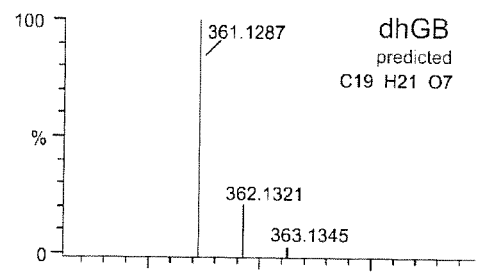
Figure 9E:
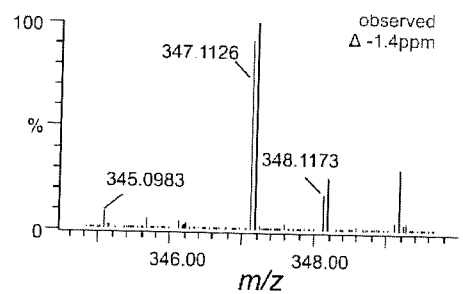
Figure 9G:
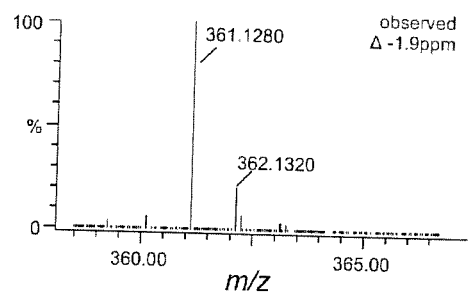

No signals for the 8-hydroxylated derivatives of NAR were visible in UV$_{290}$ traces. However, candidate peaks for both dh8HS and dhGB could be easily identified in selected ion chromatograms from the MS data (FIG. 8B). The accurate masses and isotope models matched the predictions for the specific compounds (FIGS. 9 D and E), with only one plausible candidate signal being detected for each compound.

Biofermentation Using 3'-Hydroxylated Flavone LUT as Fed Substrate

LUT differs from API by a hydroxyl residue at the 3' position of the ring B (FIG. 1). Some methoxylated derivatives of LUT occur in O. basilicum. Notably, these compounds are substituted at position 6, but not at position 8 of the backbone.

Figure 11:
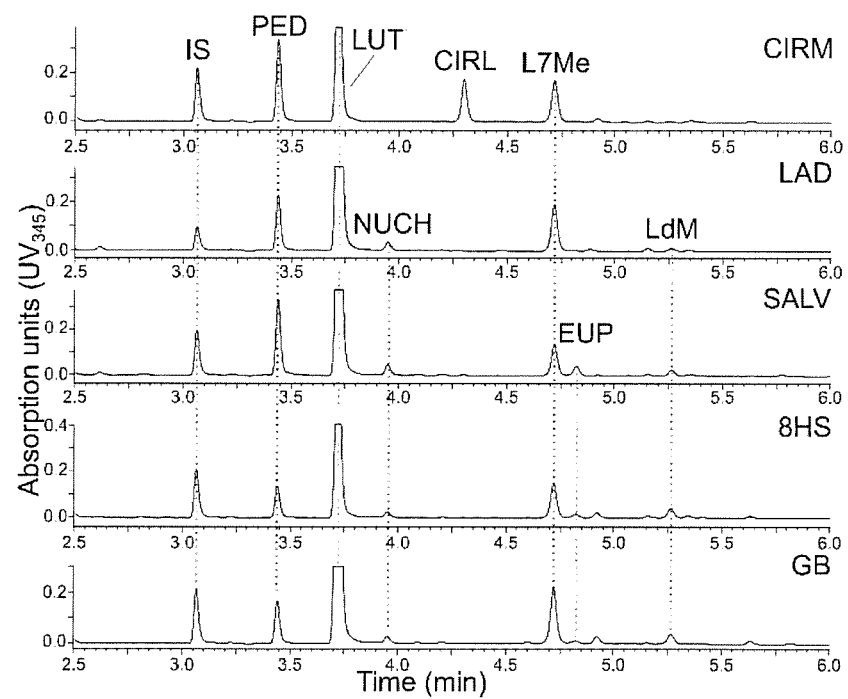
FIG. 11. Biofermentation of luteolin by the constructed yeast strains. $UV_{345}$ chromatograms of extracts from whole cell suspensions. Strains are indicated in the upper right corner. Vertical lines connect the same metabolites across strains. IS: internal standard quercetagetin. All other abbreviations as in text.
Figure 12A:
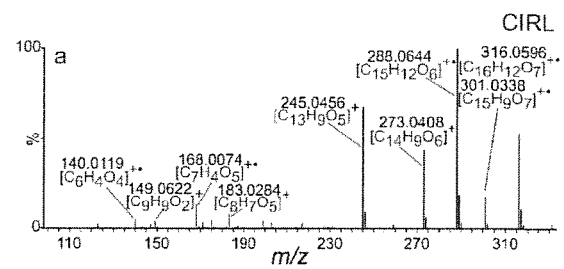
FIG. 12A-E. Identification of biofermentation products with luteolin as fed substrate. A-D, MS spectra of CIRL, NUCH, EUP, and PED; E, overlaid UV spectra of PED and (for comparison) L7Me. Note the peak at 282 nm that is characteristic of 6-hydroxylated flavones.
Figure 12B:
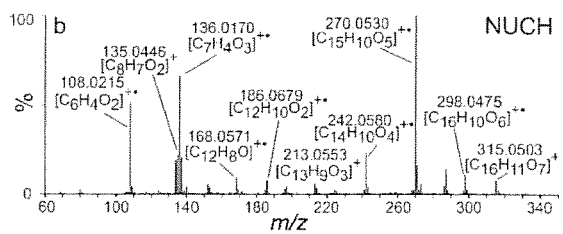
Figure 12C:
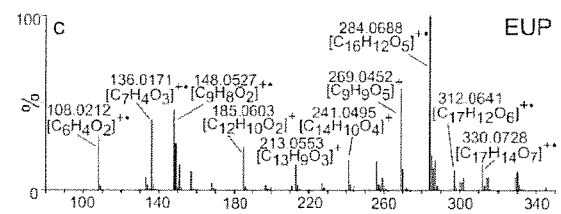
Figure 12D:
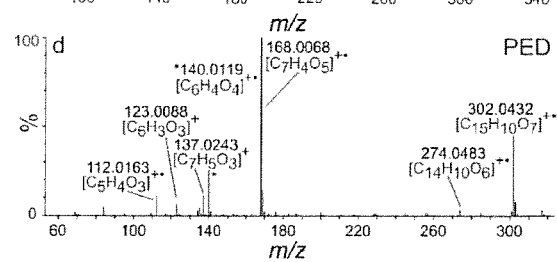
Figure 12E:
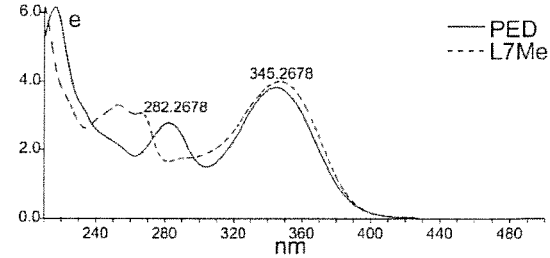
Figure 13:
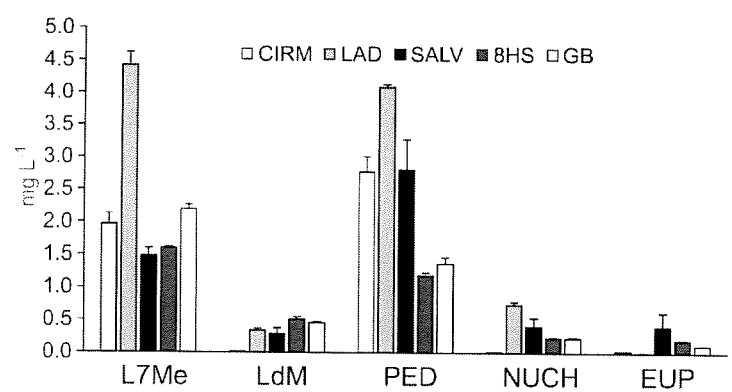
FIG. 13. Flavone accumulation in five yeast strains fed with luteolin as substrate. Abundances of L7Me, LdM, PED, NUCH, EUP are reported after two days of fermentation.

The first pathway intermediate, 7-methylluteolin (L7Me), was readily detectable in UV$_{345}$ traces of all five strains (FIG. 11, FIG. 12, FIG. 13). The 7,4'-dimethylated LUT also accumulated in considerable amounts in all but the CIRM strain. All five strains accumulated high amounts of pedalitin (PED), the 3'-hydroxylated derivative of S7Me (FIG. 6, FIG. 12, FIG. 13), suggesting that the downstream conversion of this intermediate is slower than its production. Its titers reached 2.76-4.08 mg·L$^{-1}$ in the CIRM, LAD and SALV strains, and were lower in the 8HS and GB strains. In the CIRM strain, accumulation of cirsiliol (CIRL, 3'-OH-CIRM) reached 1.74±0.15 mg·L$^{-1}$. Nuchensin (NUCH), the 3'-hydroxylated analog of LAD, reached a final titer of 0.74±0.04 mg·L$^{11}$ in the LAD strain but was also incompletely converted in the SALV, 8HS and GB strains, where it was present at 0.22-0.40 mg·L$^{-1}$. In the SALV strain, eupatorin (EUP, 3'-OH-SALV) accumulated at a final concentration of 0.40±0.22 mg·L$^{-1}$. The concentration of EUP in the 8HS and GB strains was lower in comparison to the SALV strain even though the downstream conversion to 8-hydroxylated derivatives was negligible (FIG. 13). Signals with accurate masses and isotope models matching those predicted for 3'-OH-8HS and 3'-OH-GB were detectable in selected ion chromatograms (not shown). While there was only one plausible candidate peak for 3'-OH-GB, two candidate 3'-OH-8HS signals with very similar retention times and accurate masses matching the expected formula were detected. As those signals were specific to this strain and substrate, it is possible that more than one product is formed.

The distribution of LUT and its fermentation products was analyzed in the SALV strain. Approximately equal proportions of LUT were present in the cells and the culture media (Table 3). Similar distribution was observed for L7Me and EUP. LdM was enriched in cells. Both PED and NUCH were enriched in the culture medium.

Biofermentation Using Flavonol KAEM as Fed Substrate

Figure 14:
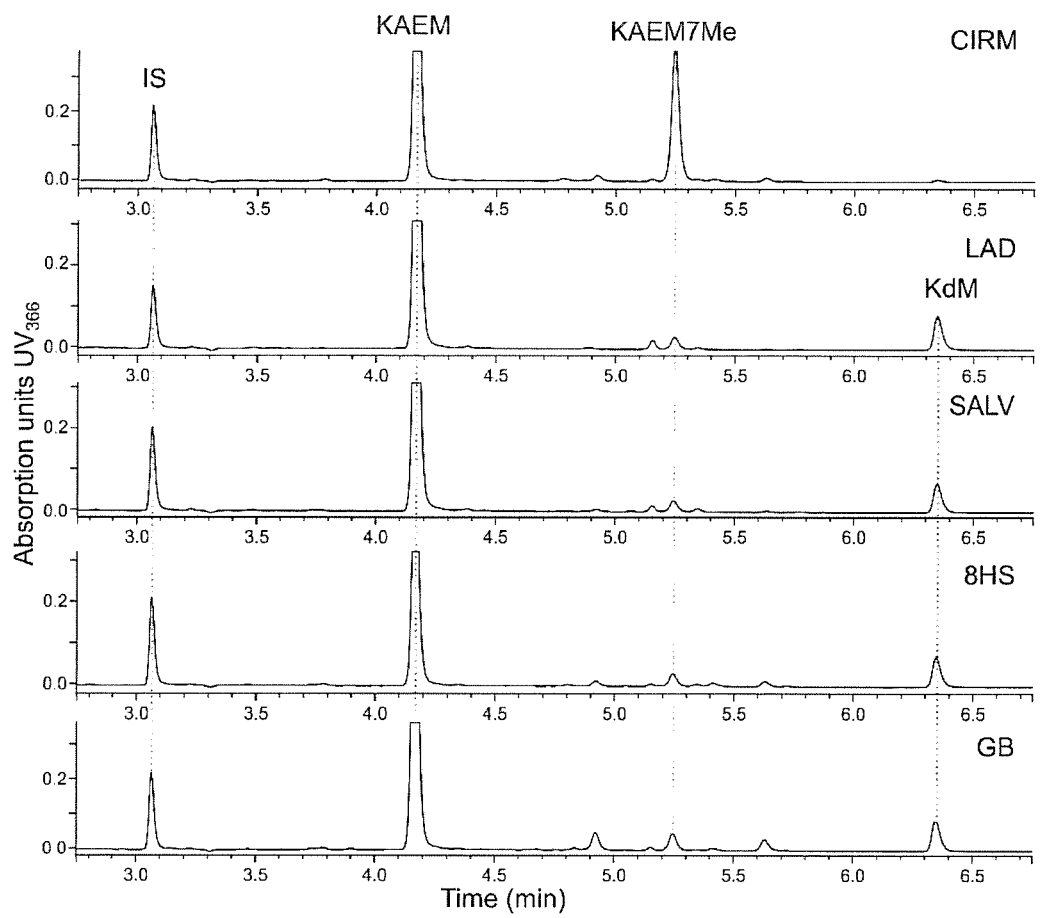
FIG. 14. Chromatograms of biofermentation products of kaempferol with five constructed strains. UV chromatograms (at 366 nm) of extracts from whole cell fermentation suspensions. The strains are indicated in the upper right corner. Vertical dotted lines connect the same metabolites across strains.
Figure 15:
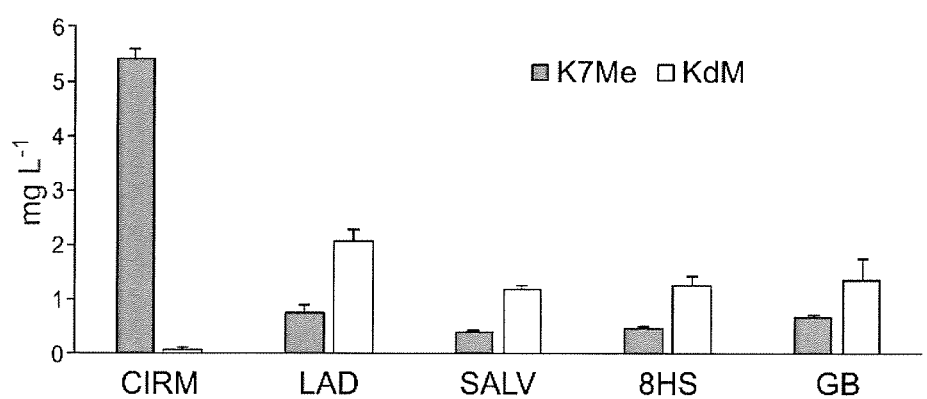
FIG. 15. Flavonoid accumulation in five strains with kaempferol as fed substrate. Abundances of K7Me and KdM are reported after two days of fermentation. Strains are shown on the X-axis, legend indicates compounds.
Figure 16A:
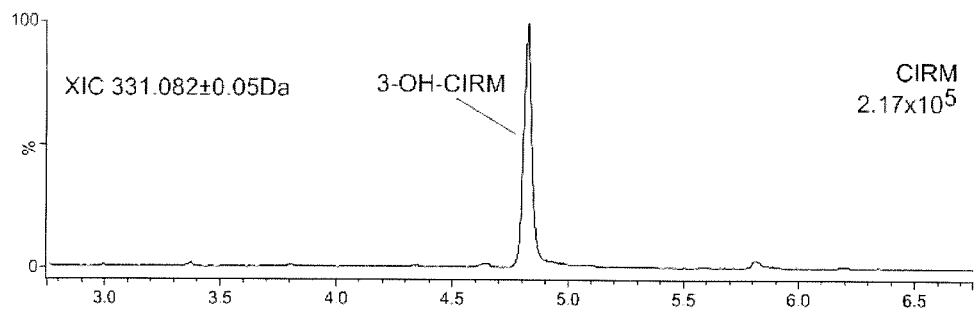
Figure 16B:
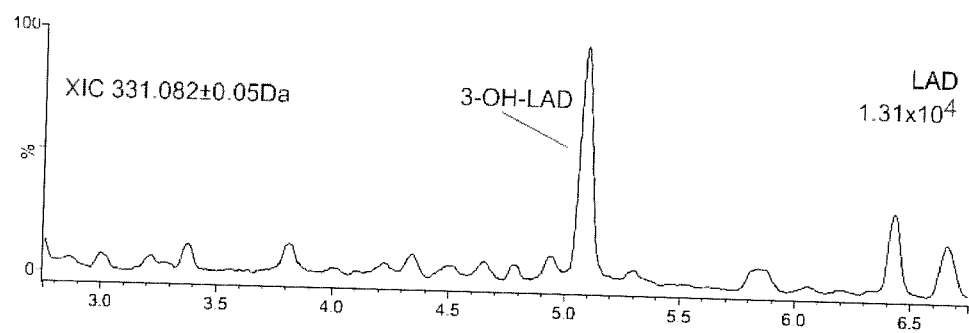
Figure 16C:
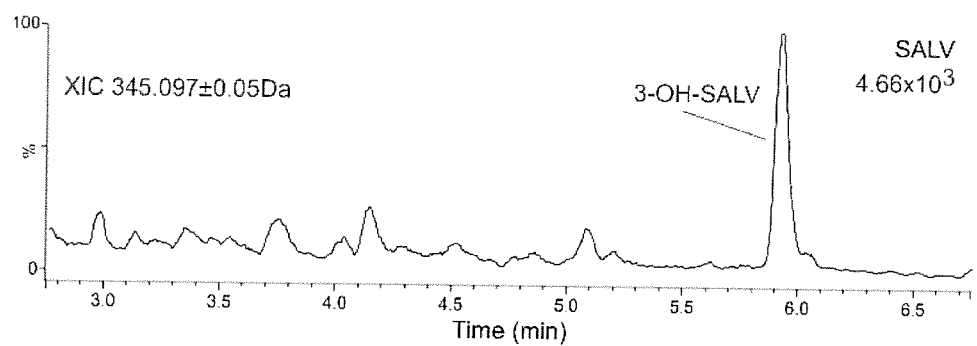

In comparison to flavones, flavonols carry an additional hydroxyl moiety at position 3 (FIG. 1). Flavonols have not been reported to accumulate in sweet basil's trichomes. In our fermentation system utilizing KAEM as fed substrate, the two abundant and easily detectable products were kaempferol-7-methyl ether (K7Me), which was present in all strains and most abundant in the CIRM strain, and kaempferol-7,4'-dimethyl ether (KdM) which was present in considerable amounts in all but the CIRM strain (FIG. 14, FIG. 15). Evaluation using the MS data revealed that a signal with the accurate mass corresponding to that of hydroxylated CIRM. was present in the CIRM strain (FIGS. 16 A, D and E). A signal with the same accurate mass but a different retention time (and thus likely representing 3-OH-LAD) was present in LAD strain (FIGS. 16 B, D and F). Its intensity was lower than that of putative 3-OH-CIRM. An even weaker signal with the accurate mass corresponding to 3-OH-SALV was present in the SALV strain (FIGS. 16 C, G and H). Under the applied cell growth and flavonoid analysis conditions, no promising signals with accurate masses corresponding to hydroxylated 8HS and GB were detected.

The localization of KAEM and its bioconversion products was analyzed in the SALV strain. Similarly to other mono- and dimethylated, 6-unsubstituted derivatives of fed substrates in this study, KdM and K7Me were enriched in cells (Table 3). About 50% of KAEM found in extracts from whole cell suspension was recovered from yeast cells.

Discussion

Faster Cell Growth Outweighs the Benefits of Selection Medium

Our results indicate that use of rich medium both affords higher overall flavonoid yield and is suitable for obtaining acceptable flavonoid composition, especially with extended cultivation time. The benefits of the higher cell growth rate seem to outweigh any reduction in biosynthesis rate due to plasmid loss. The comparison between the shake flasks and conical tubes as growth vessel showed that both the cell growth and the performance of the oxygen-dependent ObF6H-1 are reduced in cells growing in tubes. The latter conclusion is based on high relative abundance of 6-unsubstituted byproducts GENK and AdM in RT cultures of the SALV strain. The use of conical tubes enables an increase in throughput (replicates/conditions). The modification of growth conditions, e.g. shaking under angle or use of air-permeable caps, is also beneficial.

Analysis of flavonoid production over six days revealed that the yeast cells maintained biosynthetic activity during this time period.

Flavone Production Using API as Fed Precursor: Enzymes Perform Well and in Accordance with Biochemical Properties with their Native Substrate The product profiles obtained with API as fed precursor largely reflected the in vitro biochemical properties of the employed enzymes. The small amounts of byproducts observed with the CIRM strain are due to the regiospecificity of ObFOMT4, which is a highly specialized F6OMT and which therefore had only one substrate it could be active with (S7Me). In the LAD, SALV and derived strains, the permissive F4'OMTs, ObFOMT3 and ObFOMT5, could act upon an additional substrate (GENK) yielding the byproduct AdM. Notably, the relaxed substrate specificity of ObF6H-1 was beneficial for the product profile as it allowed for the 6-hydroxylation and thus partial redirection of the formed AdM in those strains.

Production of Diverse Compounds Using Alternative Substrates is Limited by the Substrate Specificities of Both FOMTs and Hydroxylases One of the goals of the present study was to establish whether and how the enzymes isolated from basil act upon alternative substrates. Such precursor-directed biosynthesis is a successful approach for the biotechnological production of novel compounds, which critically depends on the plasticity of the employed enzymes. Basil FOMTs methylate a variety of flavonoids in vitro while showing strong preference for their physiological substrates. The basil F6H is active with several flavonoid classes including flavanones and flavonols. The basil F8H was only tested with basil flavones and exhibited significant activity only with SALV. Based on these biochemical studies, the strains would be able to produce at least some amounts of 6-hydroxylated, methoxylated derivatives of LUT, NAR, and KAEM.

As expected from data collected earlier in vitro, the accumulation of 7- and 7,4'-O-methylated derivatives was readily detectable with all fed precursors and in all relevant strains. ObFOMT1 is only moderately active with NAR in vitro. This appears to be relevant for the whole-cell setup as the overall flavonoid flux (estimated as the sum of product abundances) is considerably lower for NAR than for API and LUT for each strain. KAEM was not previously evaluated but appears to be a good substrate for ObFOMT1. With NAR and LUT as fed precursors, the abundance of the dimethylated byproducts NdM and LdM is lower than that of the 7-monomethylated derivatives SAK and L7Me, respectively. This pattern is due to the low activity of basil F4'OMTs ObFOMT3/5 with NAR and LUT. The sensitivity of these FOMTs to the 3'-OH residue and the non-planar flavanone backbone also leads to accumulation of C7Me and PED. The high accumulation of 7-O-methylated derivatives with alternative substrates is also indicative of insufficient 6-hydroxylation rates by basil F6H.

Unequal Distribution of Products and Intermediates

Our study revealed unequal distribution of the flavonoid pathway intermediates and products in the various strains, with strong intracellular enrichment of a number of compounds. S7Me and LAD as well as their dihydro- and 3'-OH analogs presented a notable deviation from the norm with their medium-localized fraction being substantially higher compared to other methylated flavonoids. Indeed, our data suggest that the free 6-hydroxyl residue might be the structural feature shifting the equilibrium towards the extracellular enrichment.

The method often used for product retrieval involves mixing the cell suspension with solvent and subsequent cell removal by centrifugation. In our hands, this procedure retrieves both intra- and extracellular flavonoids. Extracellularly accumulated products can be collected with the spent medium during nutrient replenishment.

Example 2. Optimization

The SALV strain and its derivatives (8HS and GB strains) were constructed using ObFOMT3 as a bifunctional F6/4'OMT. Based on substrate specificities, another suitable enzyme combination is ObFOMT4 and ObFOMT3, where LAD formed from S7Me by ObFOMT3 is 6-O-methylated by ObFOMT4, and CIRM formed by ObFOMT4 is converted to SALV by ObFOMT3.

In addition, overexpression of ObF6H-1 permits a higher 6-hydroxylation rate to capture the nascent GENK and reduce the formation of AdM. Optimization of the downstream conversions of API leads to grafting of the present system into yeast strains optimized for the production of NAR, which can be converted into API in a single enzymatic step. For example, the reaction is catalyzed by a flavone synthase (FNS), such as a FNSII=CYP93B enzyme isolated from basil (e.g. CYP93B23; Berim and Gang 2013) or an oxoglutarate-dependent FNS I (mostly occurring in Apiaceae).

The use of co- and polycultures is a very useful tool for optimization of the strains presented here. One or more of the strains presented herein are co-cultured with the yeast cells expressing just basil F6H to achieve a relative increase in the abundance of 6-substituted products. In addition, the inclusion of relevant transporter proteins enables enhanced production of specific compounds or (re-)direction of flux through the flavonoid network in a fermentation system.

In view of the high abundance of intermediates, pathway balancing and/or alternative catalysts are employed to increase the yields of the target products with precursors other than API. An alternative F7OMT is SaOMT-2 from *Streptomyces avertimilitis* with high relative activity with NAR, KAEM and quercetin. NAR 7OMT from rice is also suitable. An alternative F4'OMT is ShOMT2 from *Solanum lycopersicum*. This enzyme is highly active with quercetin-7-methyl ether and is thus converts the derivatives of both LUT and KAEM. SOMT-2 from soybean catalyzes the 4'-O-methylation of NAR derivatives. Alternative F6H enzymes are CYP82D66 from peppermint (which possesses somewhat broader substrate specificity compared to ObF6H-1), F6H from soybean and F6H from *Scutellaria baicalensis*.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A recombinant yeast that has been transformed with
at least one heterologous plant gene encoding a flavonoid ring A hydroxylase having at least 70% sequence identity to SEQ ID NO: 6 with flavonoid hydroxylase activity; and
at least one heterologous plant gene encoding a flavonoid O-methyltransferase having at least 70% sequence identity to SEQ ID NO: 1 with flavonoid O-methyltransferase activity.

2. The recombinant yeast of claim 1, wherein the flavonoid ring A hydroxylase is a flavonoid 6-hydroxylase (F6H) and the flavonoid O-methyltransferase is a flavonoid 7-O-methyltransferase (F7OMT).

3. The recombinant yeast of claim 2, wherein the F6H is ObF6H-1 as set forth in SEQ ID NO: 6.

4. The recombinant yeast of claim 2, wherein the F7OMT is ObFOMT1 as set forth in SEQ ID NO: 1.

5. The recombinant yeast of claim 1, wherein the recombinant yeast is also transformed with at least one heterologous plant gene encoding one or more of:
a flavonoid 4-O-methyl transferase (F4OMT);
a flavonoid 5-O-methyl transferase (F5OMT);
a flavonoid 6-O-methyl transferase (F6OMT);
a flavonoid 8-O-methyltransferase (F8OMT);
a bifunctional enzyme with both flavonoid 4-O-methyl transferase and 6-O-methyl transferase activity; or
a flavone 8-hydroxylase (F8H).

6. The recombinant yeast of claim 5, wherein the bifunctional enzyme is ObFOMT3 as set forth in SEQ ID NO: 2.

7. The recombinant yeast of claim 5, wherein the at least one heterologous gene encodes a flavone 8-hydroxylase (F8H) and the recombinant yeast is further transformed with a heterologous gene encoding an Fdx-NADP$^+$ reductase.

8. The recombinant yeast of claim 1, wherein the at least one heterologous plant gene encoding a flavonoid ring A hydroxylase and/or the at least one heterologous plant gene encoding at least one flavonoid O-methyltransferase are from sweet basil (Ocimum basilicum).

9. The recombinant yeast of claim 1, wherein the recombinant yeast is a recombinant Saccharomyces cerevisiae.

10. The recombinant yeast of claim 1, wherein the recombinant yeast is selected from the group consisting of:
SALV-1 deposited with NRRL under deposit number NRRL Y-67759;
8HS-1 deposited with NRRL under deposit number NRRL Y-67760;
GB-1 deposited with NRRL under deposit number NRRL Y-67761;
CIRM-1 deposited with NRRL under deposit number NRRL Y-67762; and
LAD-1 deposited with NRRL under deposit number NRRL Y-67763.

11. A method for producing at least one hydroxylated flavonoid and/or at least one methoxylated flavonoid, comprising
culturing the recombinant yeast of claim 1 with at least one precursor of either or both the at least one hydroxylated flavonoid and/or the at least one methoxylated flavonoid, wherein the step of culturing is performed under conditions suitable to produce the at least one hydroxylated flavonoid and/or methoxylated flavonoid; and
recovering the at least one hydroxylated and/or the at least one methoxylated flavonoid produced during culturing.

12. The method of claim 11, wherein the at least one precursor is apigenin (API), naringenin (NAR), luteolin (LUT) or kaempferol (KAEM).

13. The method of claim 11, wherein the at least one hydroxylated flavonoid and/or methoxylated flavonoid is:
i) scutellarein-7-methyl ether, cirismaritin, ladanein, salvigenin, 8-hydroxysalvigenin, gardenin B and/or genkwanin if API is fed;
ii) 2,3-dihydro-cirsimaritin, 2,3,-dihydro-ladanein, sakuranetin and/or carthamidin-7-methyl ether if naringenin is fed;
iii) pedalitin, cirsiliol, L7Me and/or eupatorine if luteolin is fed; and
iv) one or more 7-methyl- and/or 7,4'-dimethylated derivatives when kaempferol is fed.

14. The method of claim 11, wherein the at least one heterologous plant gene encoding a flavonoid ring A hydroxylase and/or the at least one heterologous plant gene encoding at least one flavonoid O-methyltransferase are from sweet basil (Ocimum basilicum).

15. The method of claim 11, wherein the recombinant yeast is a recombinant Saccharomyces cerevisiae.

16. The method of claim 11, wherein the recombinant yeast is selected from the group consisting of:
SALV-1 deposited with NRRL under deposit number NRRL Y-67759;
8HS-1 deposited with NRRL under deposit number NRRL Y-67760;
GB-1 deposited with NRRL under deposit number NRRL Y-67761;
CIRM-1 deposited with NRRL under deposit number NRRL Y-67762; and
LAD-1 deposited with NRRL under deposit number NRRL Y-67763.

* * * * *